(12) United States Patent
Glossop

(10) Patent No.: US 7,840,251 B2
(45) Date of Patent: *Nov. 23, 2010

(54) DEVICE AND METHOD FOR REGISTERING A POSITION SENSOR IN AN ANATOMICAL BODY

(75) Inventor: Neil David Glossop, Toronto (CA)

(73) Assignee: Philips Electronics Ltd, Vancouver, British Columbia (CA)

( * ) Notice: Subject to any disclaimer, the term of this patent is extended or adjusted under 35 U.S.C. 154(b) by 1626 days.

This patent is subject to a terminal disclaimer.

(21) Appl. No.: 10/928,729

(22) Filed: Aug. 30, 2004

(65) Prior Publication Data

US 2005/0085793 A1    Apr. 21, 2005

Related U.S. Application Data

(63) Continuation-in-part of application No. 10/067,993, filed on Feb. 8, 2002, now Pat. No. 6,785,571, which is a continuation-in-part of application No. 09/820,796, filed on Mar. 30, 2001, now abandoned.

(51) Int. Cl.
*A61B 5/05* (2006.01)
(52) U.S. Cl. ..................................... 600/424
(58) Field of Classification Search ................ 600/114, 600/117, 145, 407, 409, 414, 424, 426, 427, 600/429, 461; 604/45–67, 529
See application file for complete search history.

(56) References Cited

U.S. PATENT DOCUMENTS

| 4,279,252 | A | 7/1981 | Martin |
| 4,697,595 | A | 10/1987 | Breyer et al. |
| 4,777,951 | A | 10/1988 | Cribier et al. |
| 4,887,606 | A | 12/1989 | Yock et al. |
| 5,042,486 | A | 8/1991 | Pfeiler et al. |
| 5,383,465 | A | 1/1995 | Lesny et al. |
| 5,391,199 | A | 2/1995 | Ben-Haim |
| 5,558,091 | A | 9/1996 | Acker et al. |
| 6,016,439 | A | 1/2000 | Acker |
| 6,036,682 | A | 3/2000 | Lange et al. |
| 6,272,370 | B1 * | 8/2001 | Gillies et al. ................. 600/411 |
| 6,272,371 | B1 | 8/2001 | Shlomo |
| 6,285,898 | B1 | 9/2001 | Ben-Haim |
| 6,285,903 | B1 | 9/2001 | Rosenthal et al. |
| 6,332,089 | B1 | 12/2001 | Acker et al. |
| 6,356,783 | B1 | 3/2002 | Hubbard, Jr. |
| 6,381,485 | B1 | 4/2002 | Hunter et al. |
| 6,616,626 | B2 * | 9/2003 | Crank et al. ................... 604/48 |

* cited by examiner

*Primary Examiner*—Anu Ramana

(57) ABSTRACT

An apparatus having an insertable portion for holding a position sensor is disclosed. The position sensor can transmit a signal indicative of its position with respect to a field generator. The insertable portion of the catheter has fiducial markings that are detectable by an imaging modality when the insertable portion is inserted into the anatomical body. The fiducial markings are asymmetrical about at least a first axis of the insertable portion. After the insertable portion has been inserted into the anatomical body, the fiducial markings can be detected to facilitate registration of the position sensor held in the insertable portion to the anatomical body. The apparatus also has a fixing mechanism for releasably fixing the insertable portion to the anatomical body. The non-symmetrical fiducial markings facilitate unambiguous registration of the insertable portion to the anatomical body. When the insertable portion is inserted into the anatomical body to a location of interest, the fixing mechanism substantially rigidly fixes the insertable portion of the catheter to a part of the anatomical body near the location of interest.

26 Claims, 23 Drawing Sheets

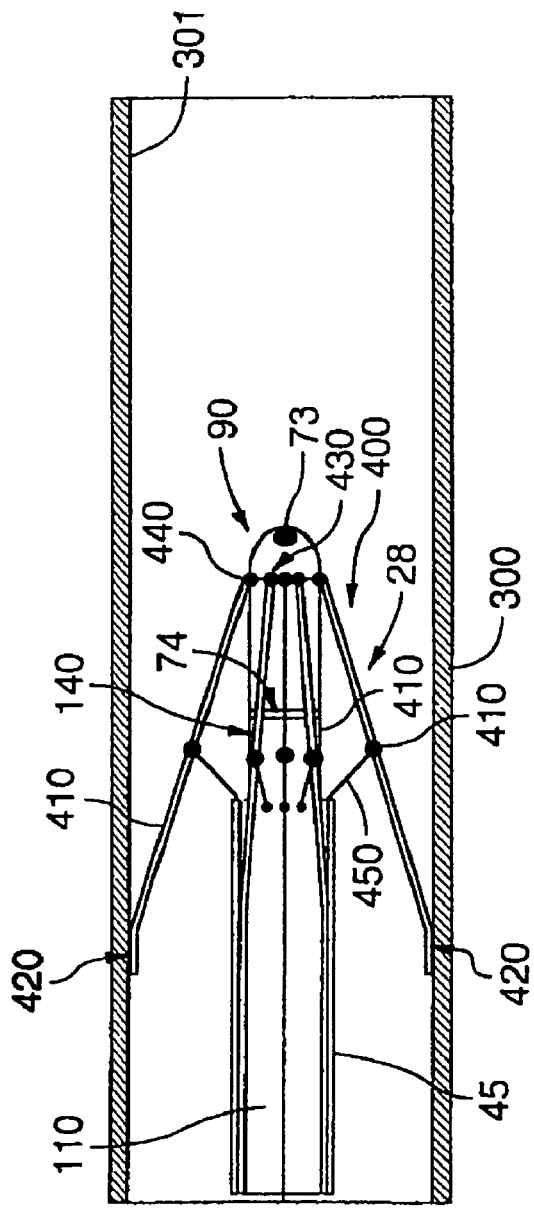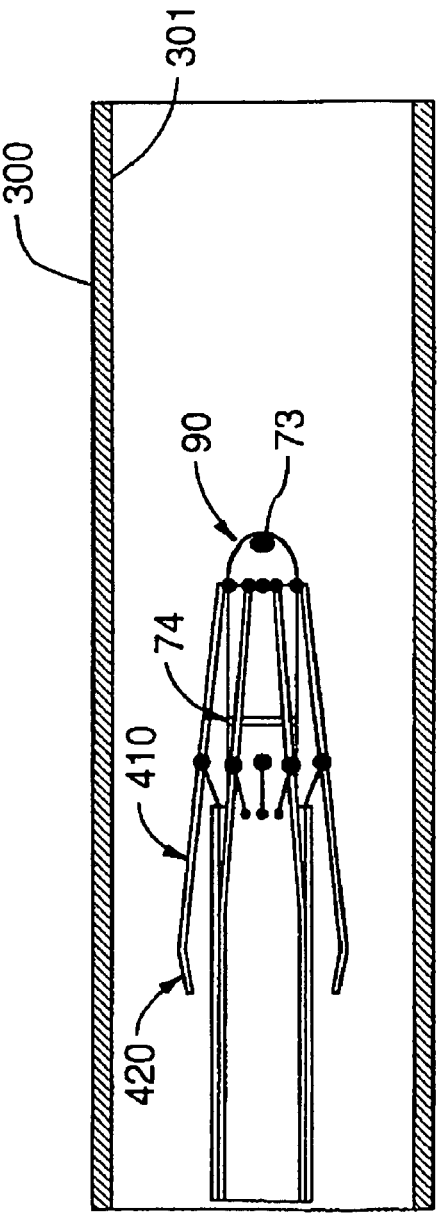

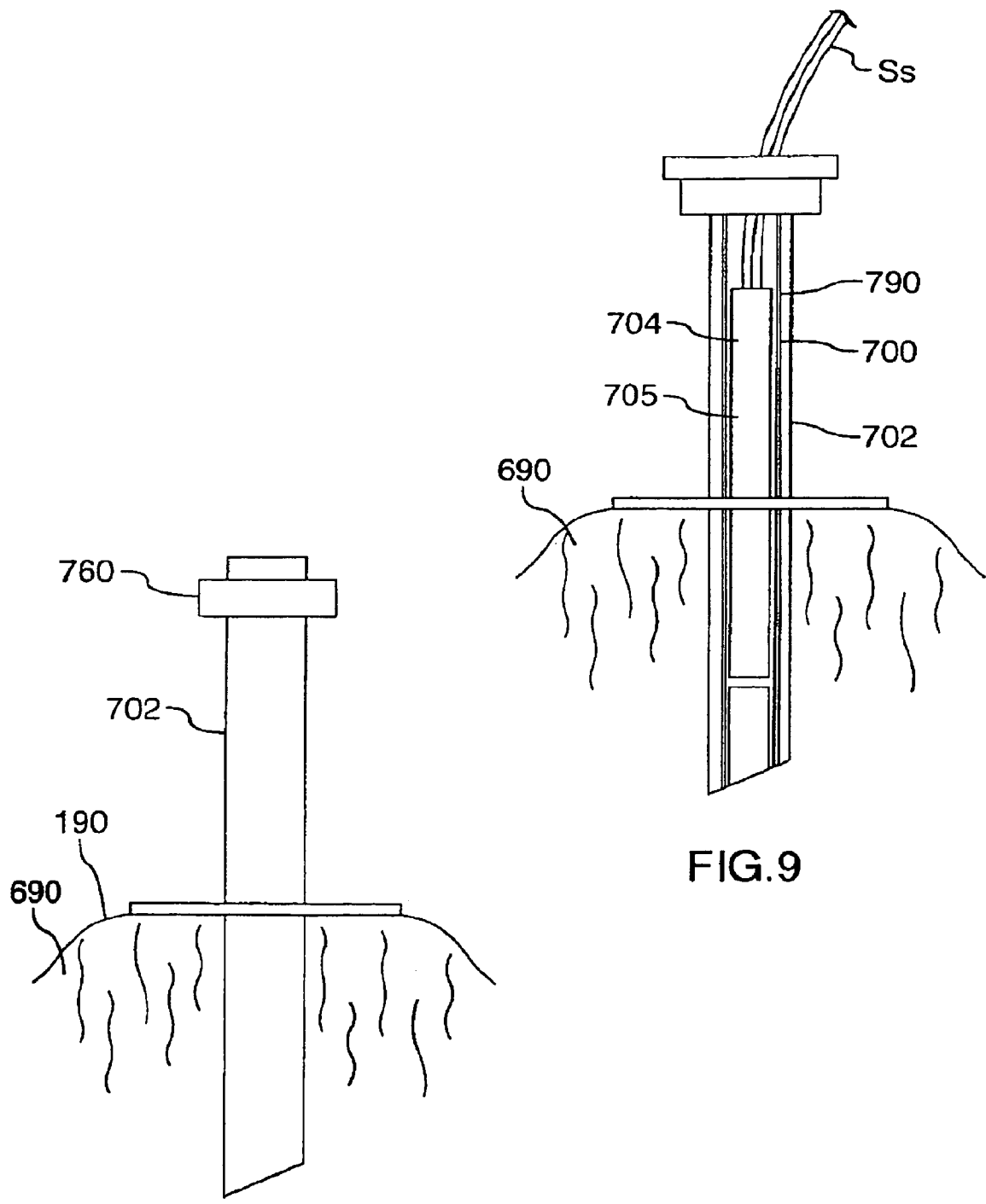

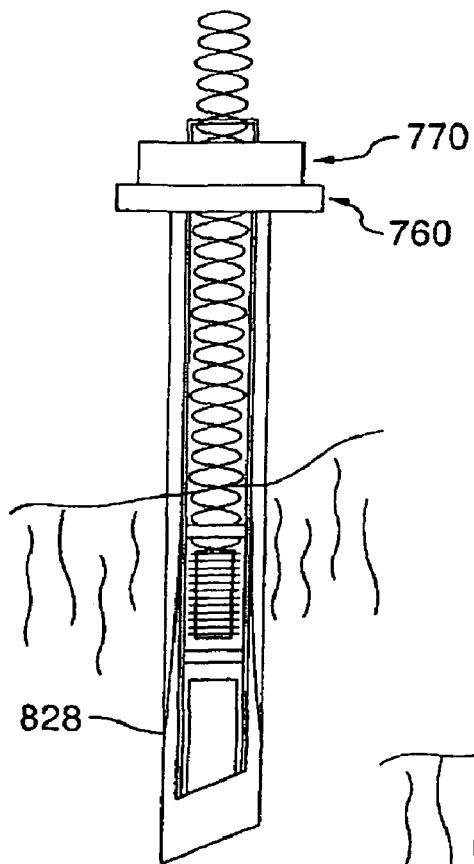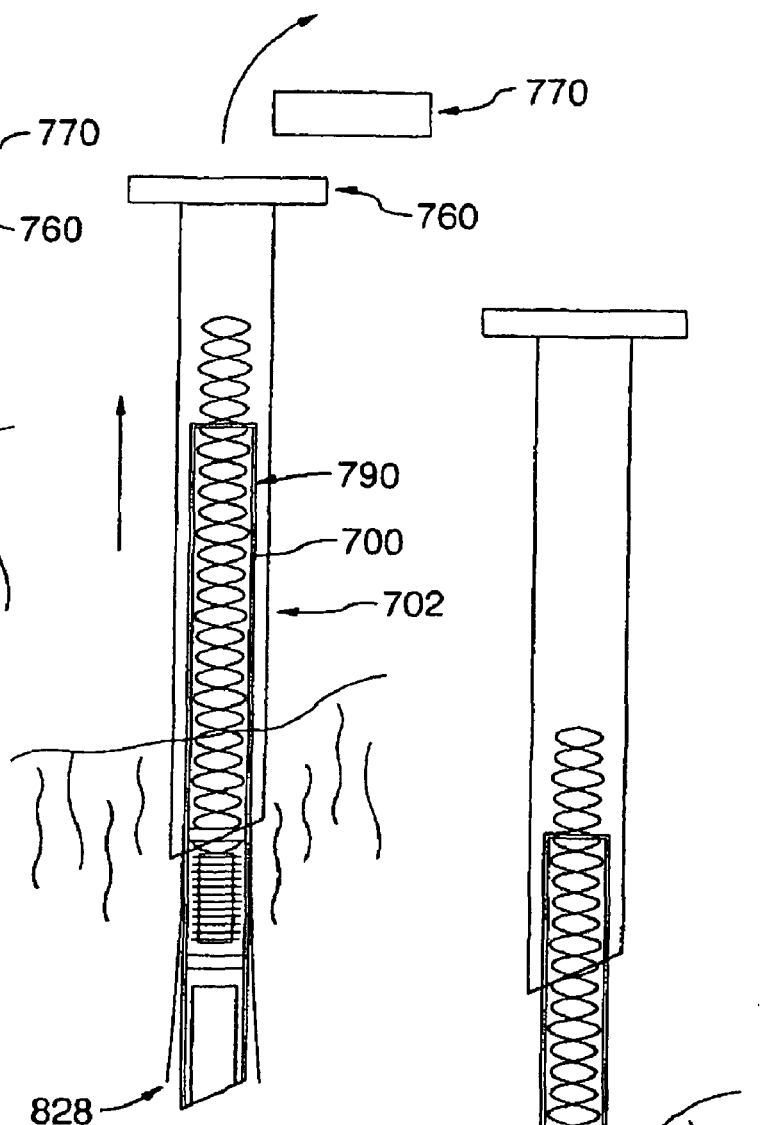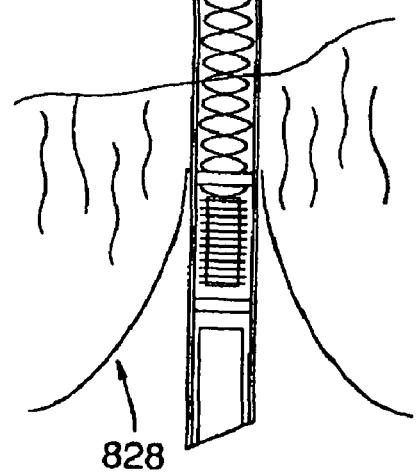
FIG.13A
FIG.13B
FIG.13C

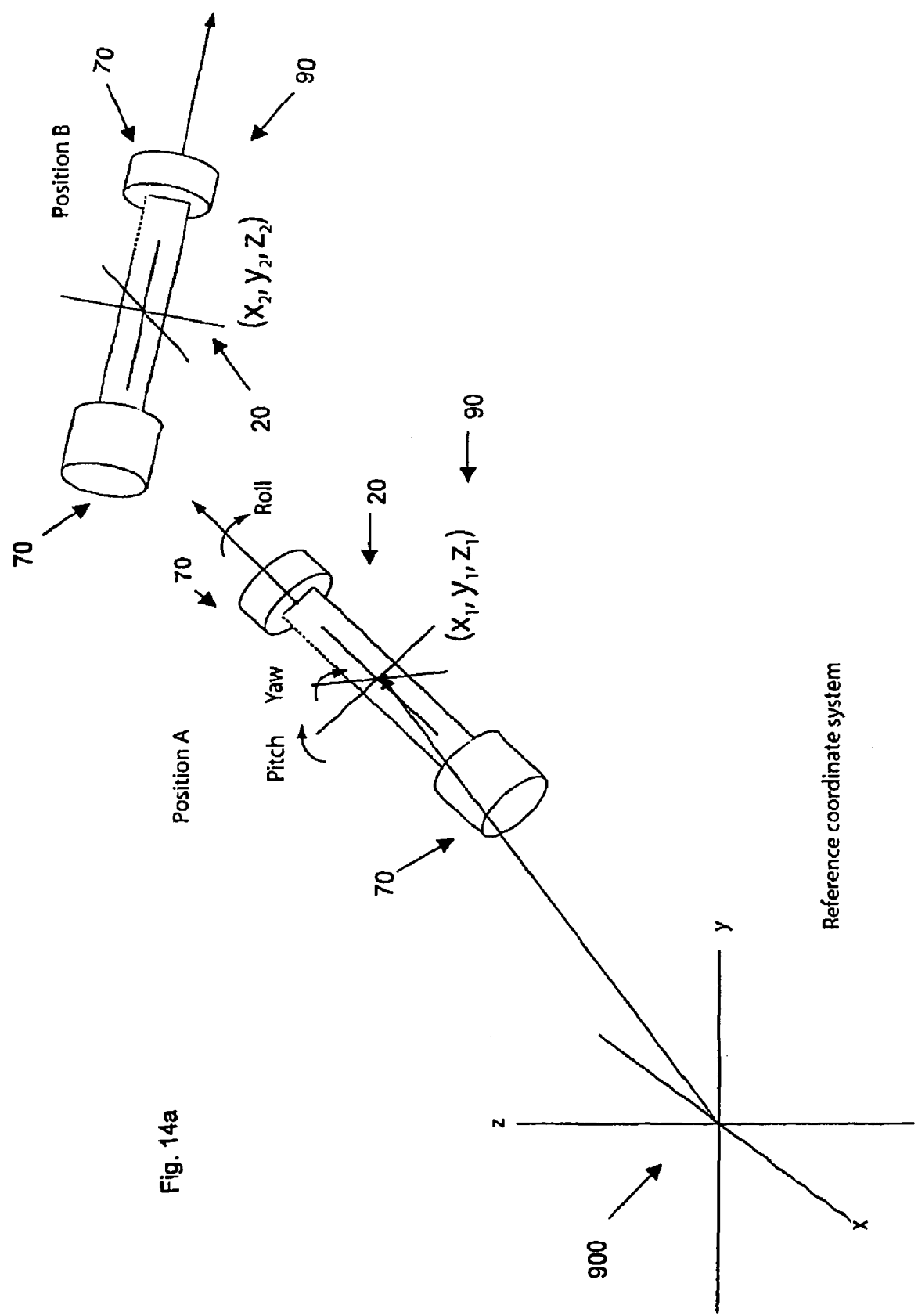

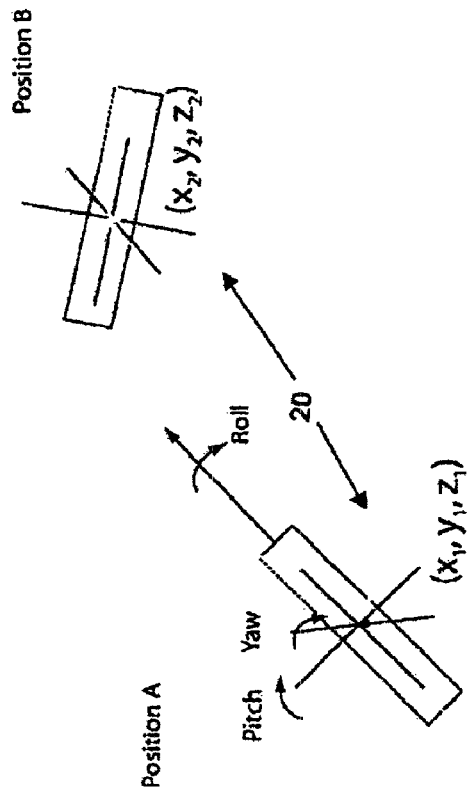
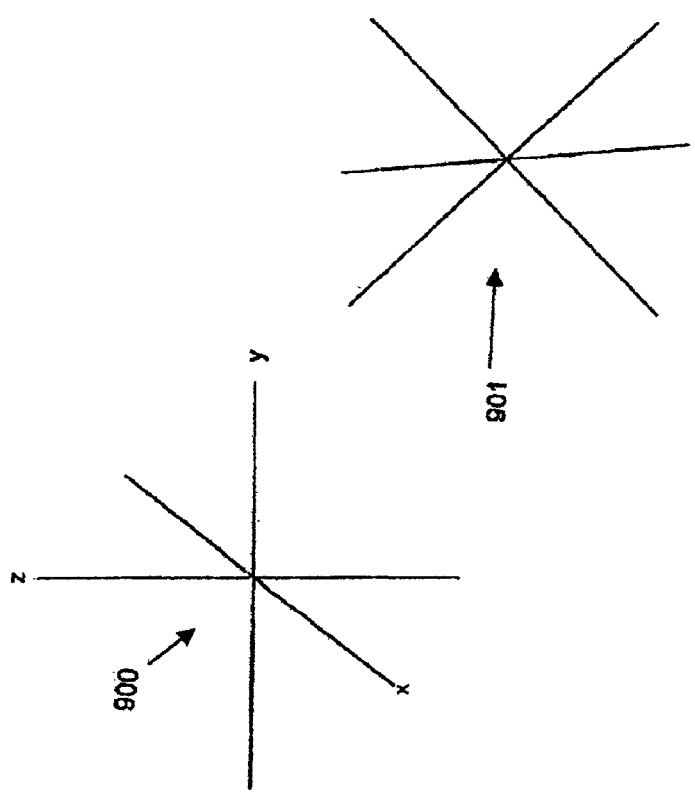
Fig. 14b

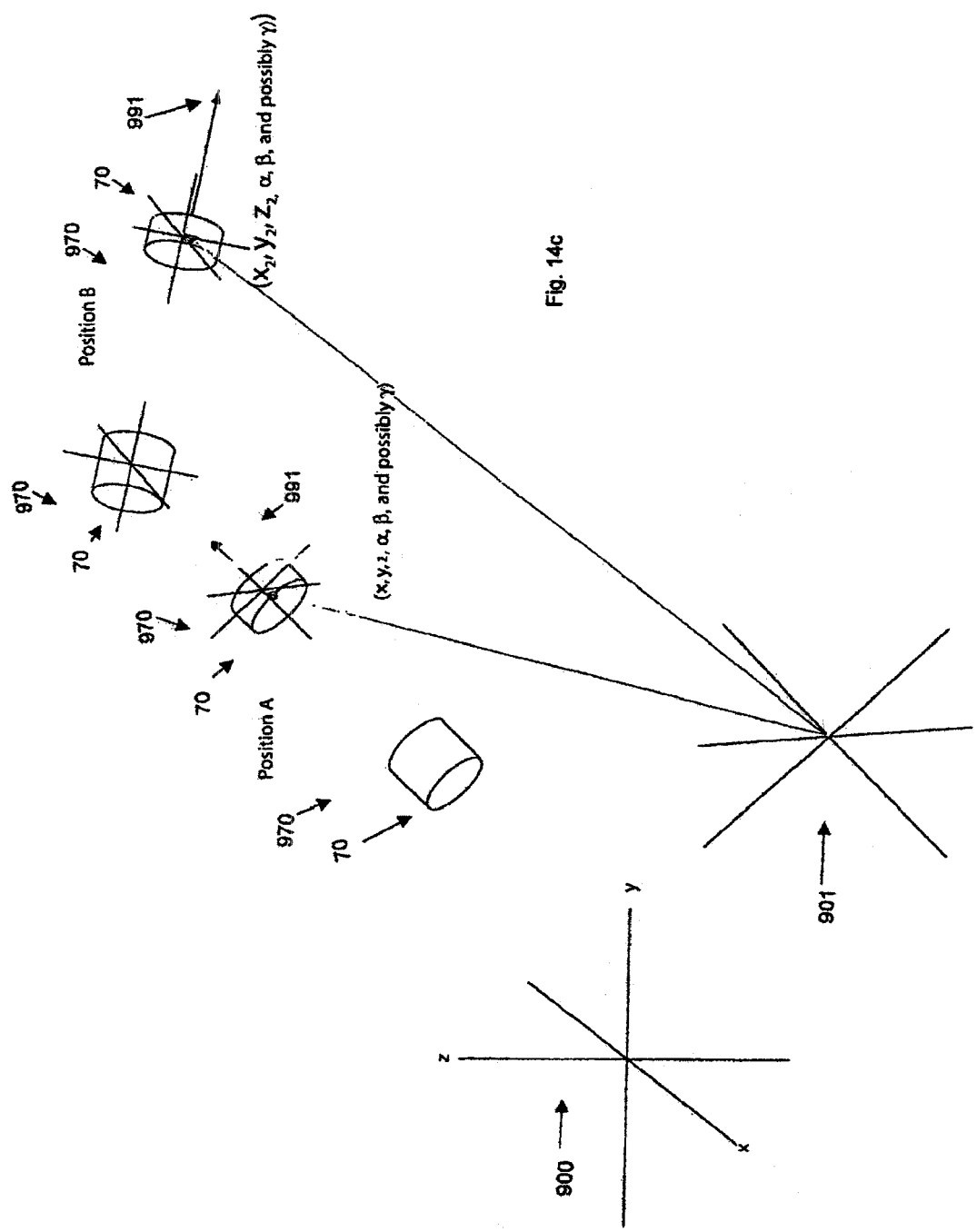

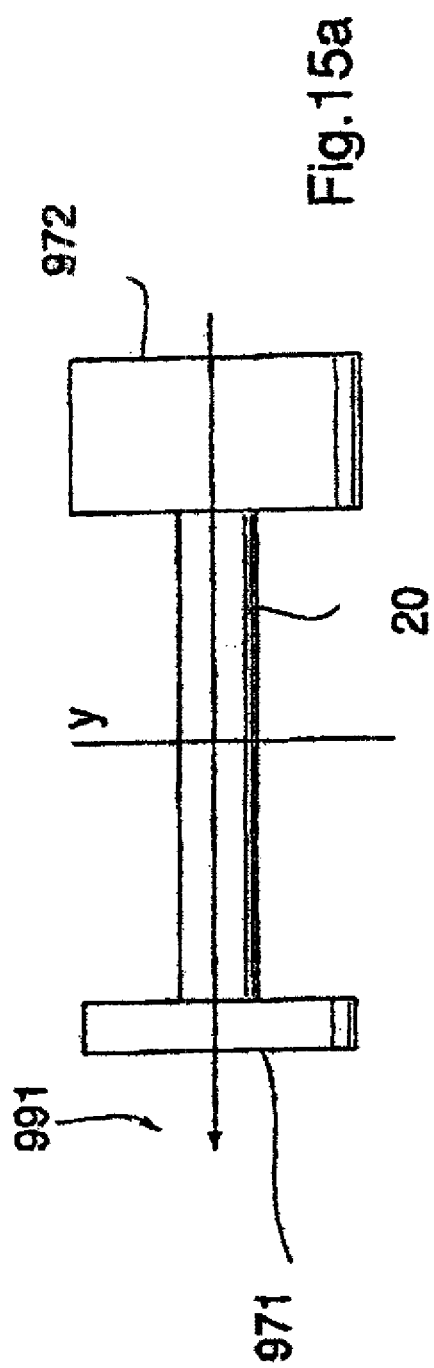
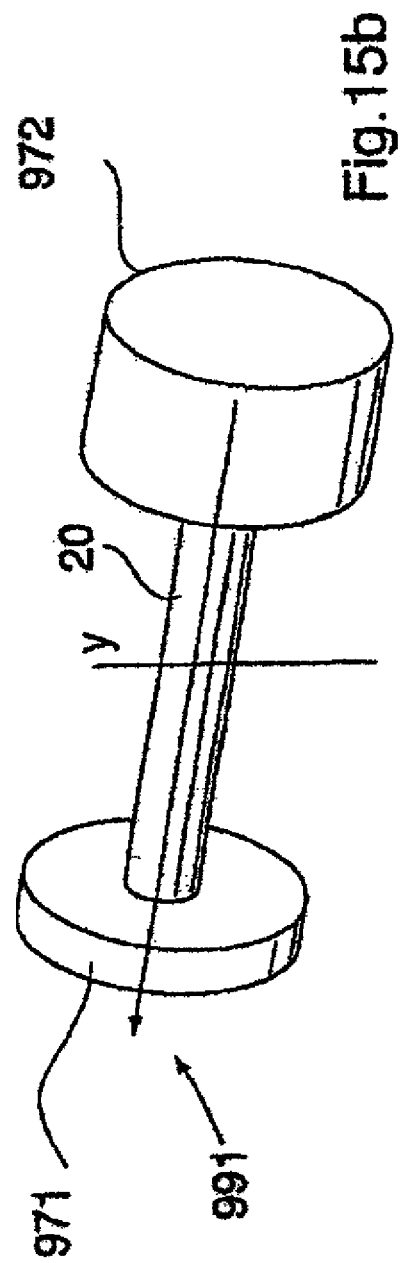

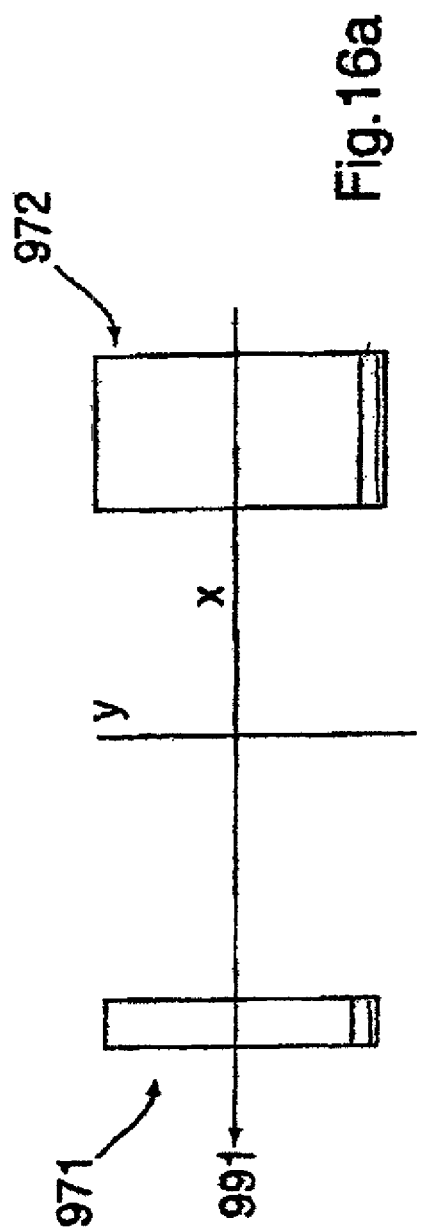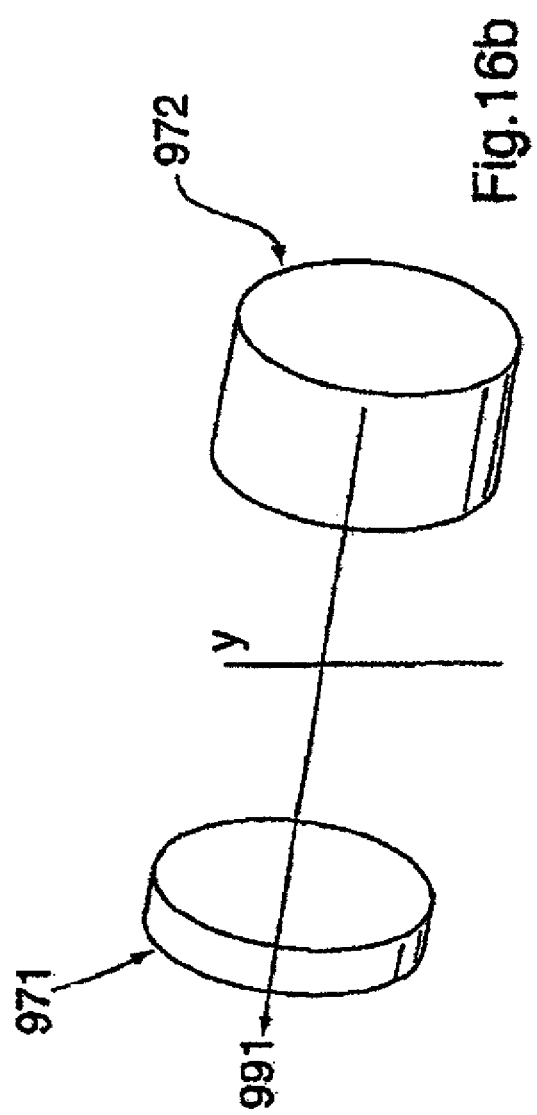

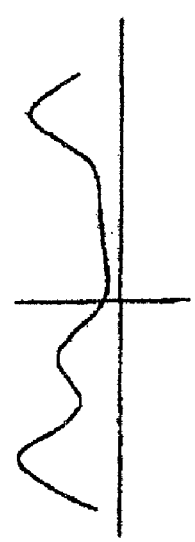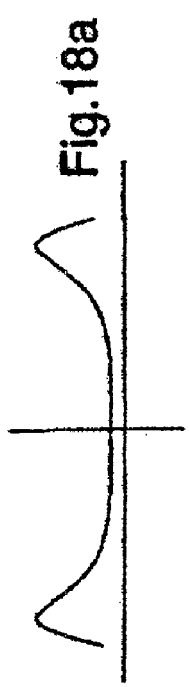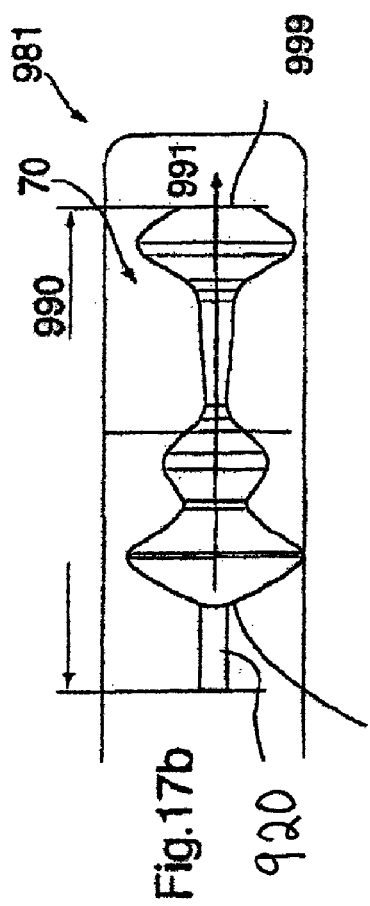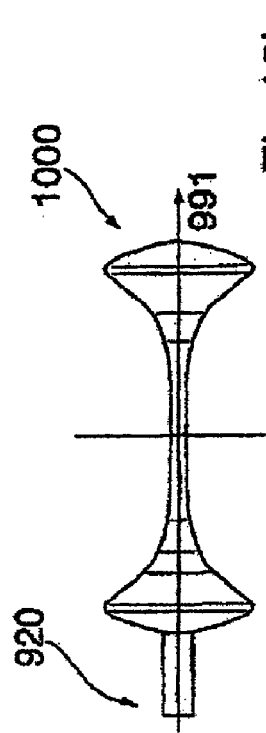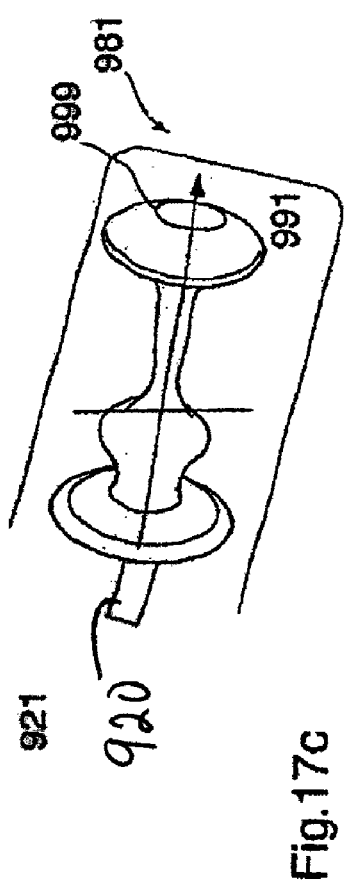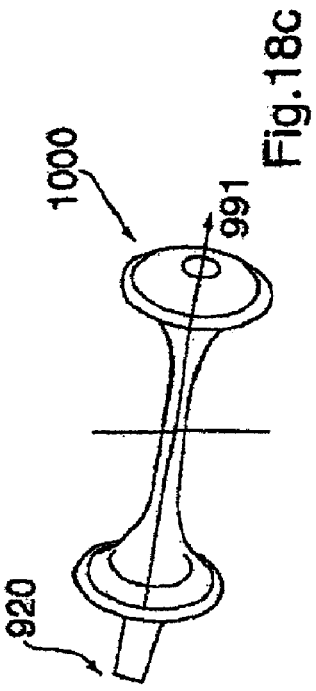

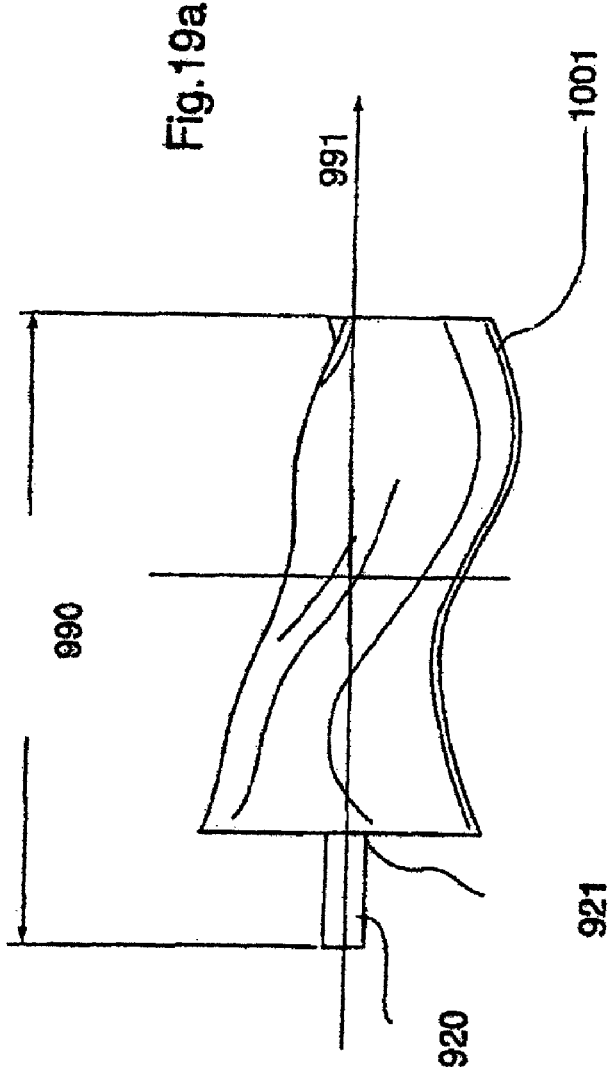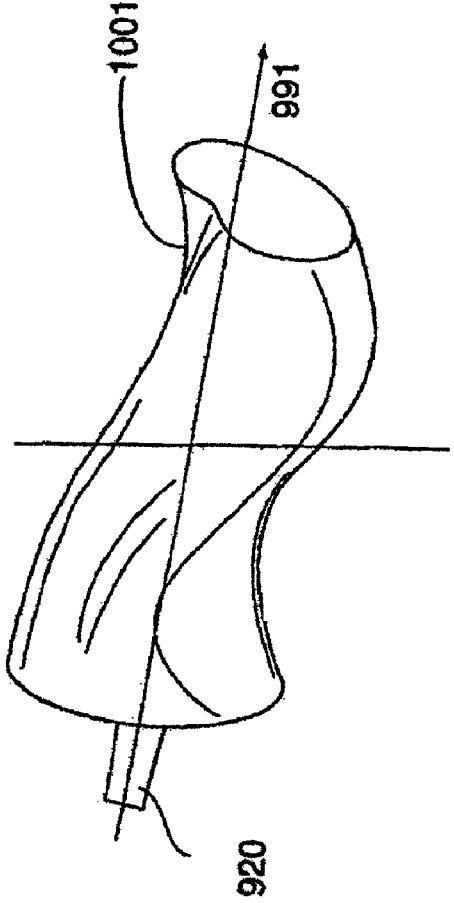

DEVICE AND METHOD FOR REGISTERING A POSITION SENSOR IN AN ANATOMICAL BODY

RELATED INVENTION

This application is a continuation-in-part of U.S. application Ser. No. 10/067,993, now U.S. Pat. No. 6,785,571, entitled "Device and Method for Registering a Position Sensor in an Anatomical Body" which is a continuation-in-part application of U.S. application Ser. No. 09/820,796, now abandoned, filed Mar. 30, 2001 and entitled "Device and Method for Registering a Position Sensor in an Anatomical Body".

FIELD OF THE INVENTION

This invention relates to devices and methods to insert position sensors into an anatomical body. More particularly, the present invention relates to a device and method for registering a position sensor inserted in an anatomical body.

BACKGROUND OF THE INVENTION

Position sensors have been increasing in accuracy and decreasing in size. This has made position sensors for use in tracking portions of an anatomical body during surgical procedures more feasible.

However, in order to accurately track areas of interest in an anatomical body, it is necessary to rigidly fix the position sensor near or at a location of interest in the anatomical body. It is also necessary to then register the position sensor with the anatomical body. A position sensor is registered to an anatomical body by correlating the position of the position sensor in the anatomical body to the determined position of the position sensor in the frame of reference. At that time, the location of interest in the anatomical body can be tracked in a fixed frame of reference, such as the operating room frame of reference, by determining the position of the position sensor.

A number of position sensors have been used in the past. Recently, magnetic sensor coils or fibre optic sensors that are reasonably small, and therefore can be substantially unobtrusively inserted into an anatomical body, have been successfully used.

However, the prior art suffers from the disadvantage that it is difficult to register the position sensors to the anatomical body. Methods for registering the position sensor in the anatomical body have included obtaining an image of the anatomical body after insertion of the position sensor and attempting to register the position sensor to the anatomical body from the acquired image. However, this suffers from the disadvantage that the position sensor is not always easily identifiable in the acquired image. Furthermore, while it may be possible to determine the position of the position sensor in the anatomical body, sufficient information may not be available from the image to determine and register both the position as well as orientation of the position sensor. Because of this, it may not be possible to determine all of the degrees of freedom, such as movement along the x, y, z axes, as well as three orientation coordinates, namely pitch, yaw and roll.

In some embodiments, it may be desirable that the position sensor be permitted to move relative to the anatomical body. However, in most cases, it is preferred that there be no relative movement between the position sensor and the location of interest in the anatomical body. Most prior art devices and methods for registering the position sensor in an anatomical body suffer from the disadvantage that there may be relative movement between the position sensor and the anatomical body. Accordingly, in addition to a method and device for accurately registering the position of the position sensor in an anatomical body, there is a need in the art for a device and method to reliably fix the position sensor to the anatomical body, thereby avoiding relative movement during the procedure. There is also a need in the art for reliable devices and methods to insert the position sensor into the anatomical body.

SUMMARY OF THE INVENTION

Accordingly, it is an object of this invention to at least partially overcome the disadvantages of the prior art. Also, it is an object of this invention to provide an improved type of device and method that facilitates simple and accurate registration of a position sensor within an anatomical body. It is also an object of this invention to provide an improved type of device and method to minimize relative movement between the position sensor and the anatomical body.

Accordingly, in one of its aspects, this invention resides in an apparatus insertable into an anatomical body, said apparatus comprising: an insertable portion for holding a position sensor that can transmit a signal indicative of its position in a frame of reference; fiducial markings on the insertable portion, said fiducial markings being detectable by an imaging modality when the insertable portion is inserted in the anatomical body and permitting the position and orientation of the insertable portion to be determined, said insertable portion substantially rigidly holding the position sensor at a known spatial position with respect to the fiducial markings; wherein the fiducial markings are non-symmetrical about at least a first axis of the insertable portion; wherein, after insertion in the anatomical body, the fiducial markings can be detected by the imaging modality to facilitate unambiguous registration to the anatomical body of the position sensor rigidly held in the insertable portion by correlating the fiducial markings detected by the imaging modality to the determined position of the position sensor in the frame of reference.

In a further aspect, the present invention resides a method of registering a position sensor to an anatomical body, said method comprising the steps of: (a) fixing a position sensor to an insertable portion of an apparatus, said insertable portion having fiducial markings thereon; (b) inserting the insertable portion of the apparatus to a location of interest in the anatomical body; and (c) detecting the non-symmetrical fiducial markings on the insertable portion of the apparatus to facilitate registration of the position sensor in the insertable portion to the anatomical body by: (c1) detecting the fiducial markings on the insertable portion; (c2) determining the position of the position sensor in a frame of reference; and (c3) registering the position sensor to the anatomical body by correlating the detected fiducial markings to the determined position of the position sensor in the frame of reference.

In a further aspect, the present invention resides a device for facilitating tracking of an apparatus in an anatomical body, said device comprising: an insertable portion for holding a position sensor that can transmit a position signal indicative of its position in a frame of reference; non-symmetrical fiducial markings on the insertable portion, said non-symmetrical fiducial markings being detectable by an imaging modality to facilitate unambiguous registration of the position sensor held in the insertable portion to the anatomical body; wherein the apparatus can insert the insertable portion into the anatomical body, and, the position signal transmitted from the position sensor indicates the position of the apparatus near the position sensor; wherein the insertable portion substantially rigidly holds the sensor at a known spatial position with respect to the fiducial markings; and wherein, after insertion of the insertable portion in the anatomical body, an image of the insertable portion can be obtained by the imaging modality, and, the position sensor can be registered to the anatomical body by correlating the fiducial markings detected by the imaging modality to the determined position of the position sensor in the frame of reference.

In one preferred embodiment, the present invention comprises fiducial markings which are not symmetrical along at least one axis. In other words, the fiducial markings are arranged such that the position, orientation and direction of pointing of the fiducial markings can be determined from the image of the fiducial markings detected by the imaging modality. This facilitates unambiguous registration by avoiding the possibility that the orientation and/or direction of the position sensor in the anatomical body is misinterpreted from the detected image of the fiducial markings.

In one aspect, the apparatus comprises a fixing mechanism for releasably fixing the insertable portion of the apparatus to the anatomical body at a location of interest. The fixing mechanism can be any type of mechanism that can releasably and rigidly fix the insertable portion to the anatomical body, such that the insertable portion will not become easily displaced during the procedure. In one embodiment, the fixing mechanism comprises a screw that screws into a part of the anatomical body, or, at least one barb that can become fixed to the anatomical body near the location of interest.

The fixing mechanism may also comprise an inflatable member that inflates when the insertable portion is at the location of interest. More preferably, the inflatable member has lobes that can inflate to fix the catheter, such as in a passageway near the location of interest, while still permitting fluid flow around the apparatus, such as a catheter, and through the passageway.

In a further preferred embodiment, the fixing mechanism comprises a plurality of movable fingers having gripping elements. The movable fingers have a collapsed configuration where the gripping elements are near the apparatus, such as a catheter or a needle, and permit insertion of the catheter into the anatomical body and near the location of interest. The movable fingers also have a deployed configuration where the gripping elements engage a surface of a passageway in the anatomical body to fix the insertable portion to the anatomical body near the location of interest, but permit fluid flow around the apparatus and through the passageway.

One advantage of the present invention is that the fiducial markings on the insertable portion permit the position, and preferably orientation, of the insertable portion to be accurately determined with respect to the anatomical body. As the position of the position sensor with respect to the insertable portion, and therefore the fiducial markings, is known, the position sensor can then be registered to the anatomical body by correlating the position of the fiducial markings in the images to the determined position of the position sensor in the fixed frame of reference.

A further advantage of the present invention is that the fixing mechanism preferably substantially rigidly fixes the insertable portion of the apparatus to the anatomical body. In this way, once the position sensor has been registered, relative movement between the anatomical body and the position sensor is decreased.

Further aspects of the invention will become apparent upon reading the following detailed description and drawings that illustrate the invention and preferred embodiments of the invention.

BRIEF DESCRIPTION OF THE DRAWINGS

In the drawings, which illustrate embodiments of the invention:

FIG. 4A is a side view of a catheter in a deployed configuration according to a further embodiment of the present invention.

FIG. 4B is a side view of the catheter shown in FIG. 4A in a collapsed configuration.

FIG. 8c illustrates the needle shown in FIGS. 8a and 8b, but with the insertable portion removed.

FIG. 9 illustrates an apparatus according to one embodiment of the invention having a needle, a stylette and the insertable portion in the form of a secondary stylette.

FIGS. 13a, 13b and 13c illustrate the deployment of the fixing mechanisms shown in FIG. 12.

FIGS. 14a, 14b, 14c and 14d illustrate the process by which the position sensor is registered using an insertable portion having fiducial markings which are not symmetrical along at least one axis according to one embodiment of the present invention.

FIGS. 15a and 15b illustrate a side view and perspective view, respectively, of an insertable portion having fiducial markings which are not symmetrical about at least one axis, according to a preferred embodiment of the present invention.

FIGS. 16a and 16b are representations of a side view and a perspective view of the detected fiducial markings for the insertable portion illustrated in FIGS. 15a and 15b.

FIGS. 17a, 17b and 17c illustrate an insertable rigid portion comprising a mantle and a sensor rigidly attached thereto with the mantle being asymmetric along at least one axis according to one embodiment of the present invention.

FIGS. 18a, 18b and 18c illustrate an insertable rigid portion comprising a mantle and a sensor rigidly attached thereto with the mantle being symmetric upon all three axes.

FIGS. 19a and 19b illustrate a side view and a perspective view of a mantle being asymmetric along all three axes such that no axis or plane of symmetry exists according to a further embodiment of the present invention.

DETAILED DESCRIPTION OF THE PREFERRED EMBODIMENTS

Figure 1A:
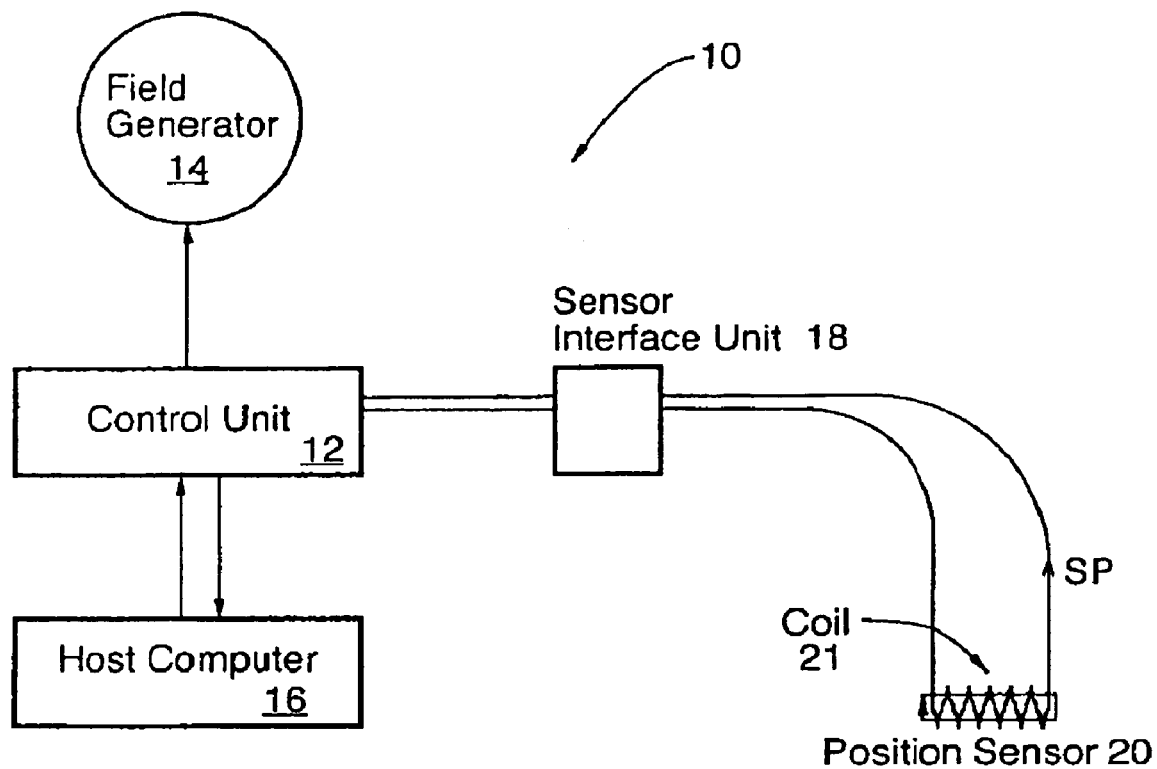
FIG. 1A is a symbolic representation of a position sensor system as known in the art.
Figure 1B:
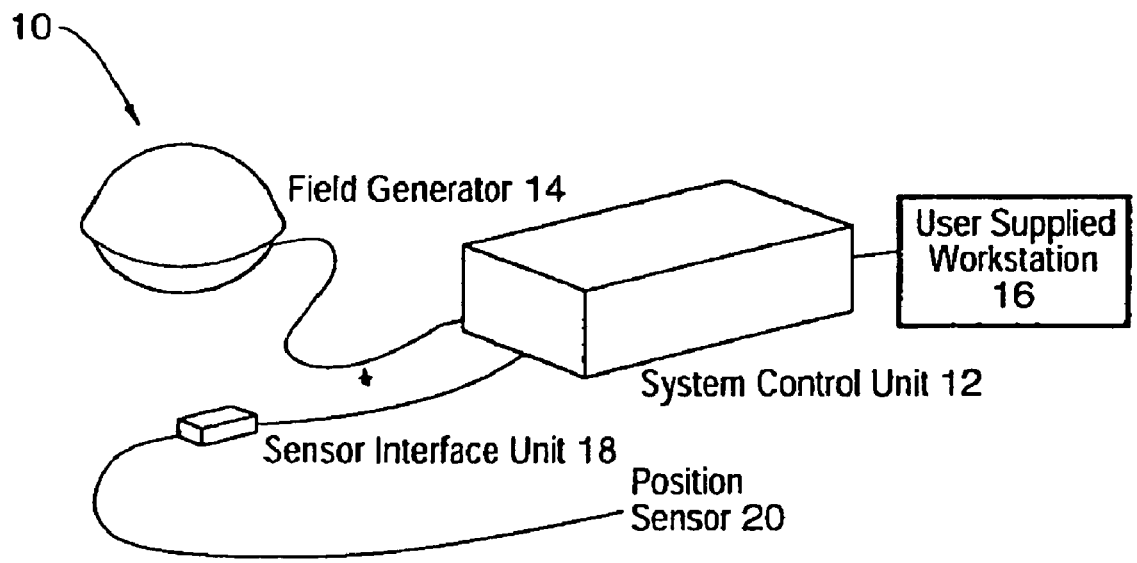
FIG. 1B is an illustration of a position sensor system as known in the art.

FIGS. 1A and 1B show a conventional position sensor system, shown generally by reference numeral 10. The system 10 comprises a control unit 12 that is connected to a field generator 14 and a host computer 16. The host computer 16 can be a user supplied work station. The field generator 14 generates a complex electromagnetic field within a frame of reference. A position sensor 20 within the frame of reference can sense the complex electromagnetic field. The system 10 also comprises a sensor interface unit 18 that interfaces the control unit 12 to the position sensor 20. It is understood that these components may be integrated together. For example, the sensor interface unit 18 may be combined with the control unit 12.

The position sensor 20 generally comprises a sensor element, such as a magnetic sensor coil 21, which reacts to, or senses, the complex electromagnetic field generated by the field generator 14. As the position sensor 20 moves in the electromagnetic field generated by the field generator 14, the sensor coil 21 generates a position signal $S_P$ that is indicative of the position of the position sensor 20. Generally, the sensor coil 21 will react to changes to both the position and orientation of the position sensor 20 in the frame of reference. In this way, the position signals $S_P$ generated by the sensor coil 21 are indicative of both position and orientation of the position sensor 20. The position signals $S_P$ are received by the sensor interface unit 18 and converted to a form which can be understood by the host computer 16.

Thus, the position and orientation of the position sensor 20 can be determined in the frame of reference of the field generator 14. The frame of reference of the field generator 14 is generally a fixed frame of reference, such as the frame of reference of the operating room.

In order for the position sensor 20 to be of assistance in tracking or determining the position and orientation of a location of interest in an anatomical body, it is necessary that the position sensor 20 be registered with respect to the location of interest in the anatomical body. In addition, it is often desirable that the position sensor 20 is fixed in some way to the anatomical body so that, once the position sensor 20 is registered to the anatomical body, the position sensor 20 will not move with respect to the anatomical body.

Figure 2A:
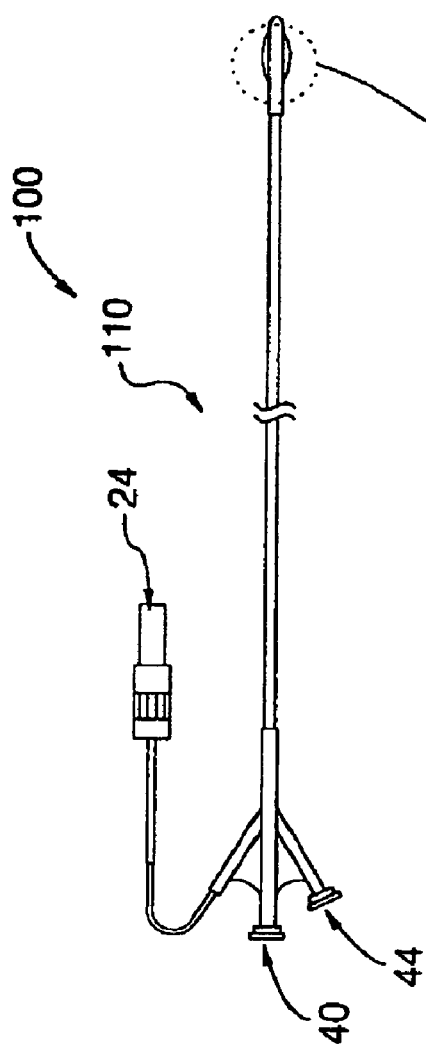
FIG. 2A illustrates an apparatus comprising a catheter having an inflatable member according to one embodiment of the present invention.

FIGS. 2A, 2B, 2C and 2D show an apparatus, shown generally in FIG. 2A by reference numeral 100, to facilitate inserting, fixing and registering a position sensor 20 into the anatomical body according to one embodiment of the present invention. The apparatus 100 in this embodiment comprises the sensor coil 21 held within an insertable portion 90. In this embodiment, the apparatus 100 comprises a catheter 110 for inserting the insertable portion 90 into the anatomical body.

The catheter 110 moves along a guidewire 60, as is known in the art. The catheter 110 will move into a passageway of the anatomical body until the position sensor 20 is near a location of interest in the anatomical body. The location of interest is the part of the anatomical body whose position is desired to be determined and tracked during a procedure.

In this embodiment, the apparatus 100 also comprises electrical leads 26 which extend from the position sensor 20, and in particular, the sensor coil 21, outwards through a plug connector 24, shown in FIG. 2A. The electrical leads 26 transmit the position signals $S_P$ from the sensor coil 21 of the position sensor 20 to the sensor interface unit 18, the control unit 12, and to the host computer 16. The plug connector 24 connects to the sensor interface unit 18 of the system 10.

The apparatus 100 also comprises a fixing mechanism, shown generally by reference numeral 28. In the embodiment shown in FIG. 2B, the fixing mechanism 28 comprises an inflatable member 30, such as a balloon, which expands radially outwards from the longitudinal axis of the insertable portion 90 when inflated. The catheter 110 also comprises an inflatable opening 44 that is used in this embodiment for providing air, or other fluid, to the inflatable member 30. It is understood that if a different type of fixing mechanism 28, other than an inflatable member 30, is used, an inflatable opening 44 may not be required or may be substituted with an alternate activation pathway or method. The catheter 110 also comprises a guide path opening 40, as is known in the art.

In operation, the catheter 110 is inserted into the anatomical body by placing the catheter 110 over the guidewire 60 at the distal end, as is known in the art. The insertable portion 90 of the catheter 110 will then be lead to a passageway near the location of interest in the anatomical body. In the preferred embodiment, once the insertable portion 90 is near the location of interest, the inflatable member 30 will be inflated by passing air through the inflatable opening 44. The inflatable member 30 will then expand radially to the sides of the passageway, thereby rigidly fixing the insertable portion 90 to the passageway near the location of interest.

Once the insertable portion 90 is fixed to a part of the anatomical body near the location of interest, an image of the location of interest can be made using a known imaging modality. It is noted that the insertable portion 90 has fiducial markings 70 which are detectable by the imaging modality after insertion of the insertable portion 90 into the anatomical body. Detection of the fiducial markings 70 by the imaging modality facilitates registration of the position sensor 20 to the anatomical body.

Preferably, the position sensor 20 is held in the insertable portion 90 so that the distance and orientation of the position sensor 20 with respect to the fiducial markings 70 will remain constant. To accomplish this, it is generally preferred that the insertable portion 90 is rigid or substantially rigid so that the distance and orientation of the position sensor 20 with respect to the fiducial markings 70 will remain substantially constant. In general, the insertable portion 90 should be as rigid as required by the particular position sensor 20 being used. For instance, if the position sensor 20 can detect movement, such as bending, then the insertable portion 90 can be less rigid, provided the position sensor 20 could compensate for this lack of rigidity by sensing this bending movement. In a preferred embodiment, the insertable portion 90 is substantially rigid so as to maintain the position and orientation of the fiducial markings 70 with respect to the insertable portion 90 substantially constant.

In a preferred embodiment, the imaging modality can comprise CT scans, fluoroscopic images and ultrasound images. When the imaging modality comprises CT scans and fluoroscopic images, the fiducial markings 70 preferably comprise a radio-opaque substance. The fiducial markings 70, as well as the insertable portion 90 and the catheter 110, should also be made from a substance that does not react with anatomical bodies. Preferably, when the imaging modality comprises CT scans and fluoroscopy, it is preferred that the fiducial markings 70 comprise tantalum.

During the procedure, the fiducial markings 70 can perform a dual purpose. Firstly, the fiducial markings assist in guiding the catheter 110 to an anatomical body near the area of interest when viewed with a fluoroscope, for example. Secondly, the fiducial markings 70 facilitate registration by quantitatively co-locating the position sensor 20 in the image with the detected position of the position sensor 20 in the frame of reference. In other words, by determining the location of the fiducial markings 70 in the image, and knowing the distance and orientation of the fiducial markings 70 with respect to the position sensor 20 which is rigidly held in the insertable portion 90 of the catheter 110, an automatic registration can be made between the determined position of the position sensor 20 using the position sensor system 10 and the determined position of the position sensor 20 using the fiducial markings 70 in the image. The fiducial markings 70 detected by the imaging modality can be used to determine the position and orientation of the position sensor 20 in the image, and therefore the anatomical body. As stated above, the insertable portion 90 is preferably rigid or semi-rigid, as required to determine the position and orientation of the position sensor 20 from the fiducial markings 70.

Figure 2B:
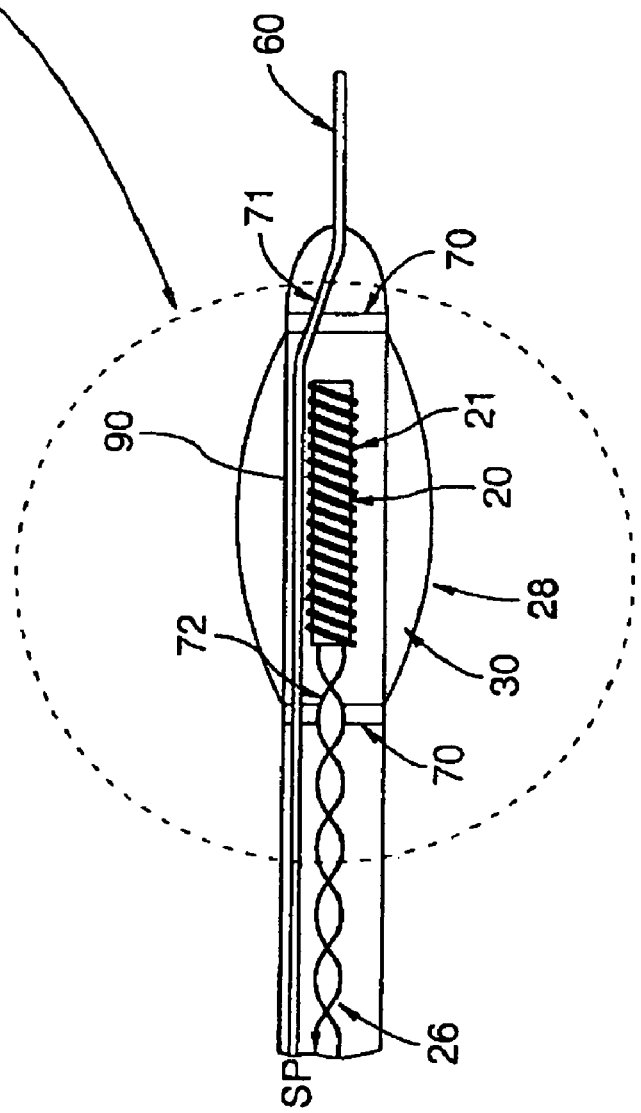
FIG. 2B is an enlarged detailed drawing of the guidewire and catheter shown in FIG. 2A.

In order to facilitate registration, it is preferred that the fiducial markings 70 comprise at least two markings 71, 72 which permit the position and orientation of the insertable portion 90 to be determined in the image. As shown in FIG. 2B, the at least two markings 71, 72 are bands around the insertable portion 90. Furthermore, in order to increase the accuracy, it is preferred that the at least two markings 71, 72 be located at opposed ends of the insertable portion 90, and preferably as far apart as possible, while remaining on the insertable portion 90. To assist in registering the position sensor 20, the shadow of the position sensor 20, such as the sensor coil 21 in this embodiment, can be used as a further marker in the image obtained by the imaging modality.

Figure 2C:
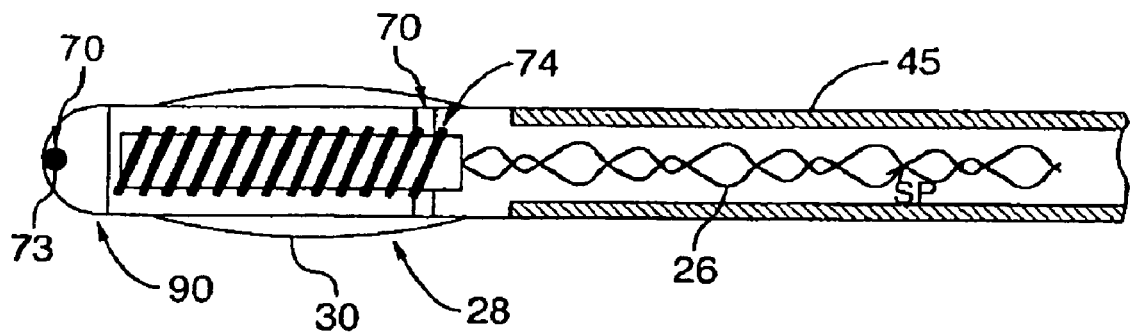
FIG. 2C is a detailed drawing of a catheter having an inflatable member according to a further embodiment of the present invention.

As shown in FIG. 2B, the at least two markings 71, 72 are bands which extend around the circumference of the insertable portion 90. In addition, the fiducial markings 70 may comprise a bead 73 as shown in FIG. 2C. A band 74 would preferably still be used in association with the bead 73 as the band 74 can be used to more easily identify the orientation of the insertable portion 90. In addition, the fiducial markings 70 may comprise a series (not shown) of beads 73, which can also be used to identify the orientation. Also, a series of bands 74 may be used to increase accuracy.

The fiducial markings 70 should have any position, orientation or shape that permits determination of the position and orientation of the position sensor 20 held by the insertable portion 90 by the imaging modality. While a number of fiducial markings 70 may be used in the insertable portion 90, at least two markings 71, 72 will generally be required to determine both the position and orientation of the insertable portion 90. If, in a particular situation, only the position and not the orientation need be determined, one fiducial marking 70 may be used. Furthermore, in some cases, the sensor element in the position sensor 20 may not be able to determine six degrees of movement. For instance, when the sensor element is a magnetic sensor element 21, as shown in FIGS. 2A, 2B, 2C and 2D, it may be difficult to determine roll using the system 10. In this case, if the position sensor 20 cannot determine roll, it is not necessary to use the fiducial markings 70 which can identify the roll orientation of the position sensor 20. Accordingly, the fiducial markings 70 may only be required to identify some of the six degrees of freedom, and may not be required for all three positions or all three orientations, depending on the particular situation. Furthermore, the fiducial markings 70 need not be two separate markings, but rather may be a single complex marking, a series of interconnected markings, or a single marking, provided some positional and/or orientational information can be obtained.

If the system 10 cannot determine all of the degrees of freedom of the position sensor 20, it may be necessary to place more than one position sensor 20 near the location of interest in order to track the motion of the location of interest in all of the degrees of freedom. It is also understood that in some situations, it will not be necessary to track all of the possible positions and orientations of the location of interest. In these situations, the fact that a particular sensor element (not shown) of the position sensor 20 cannot track one degree of freedom, such as the roll, may not adversely affect use of the position sensor 20 and may not require additional position sensors 20 to be used.

Figure 2D:
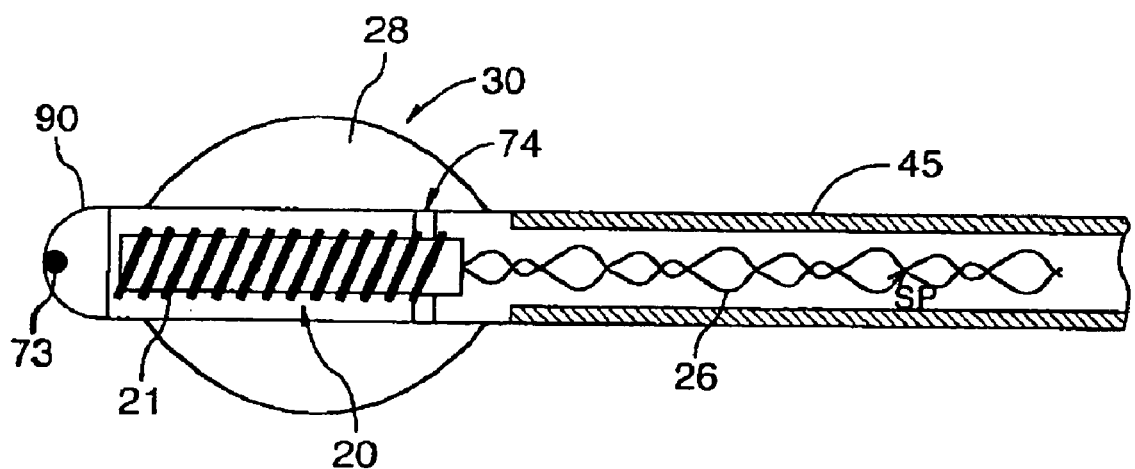
FIG. 2D is a drawing of the catheter shown in FIG. 2C with the inflatable member inflated.

FIGS. 2C and 2D also illustrate use of the inflatable member 30. In particular, FIG. 2C shows the inflatable member 30 in the deflated position, and FIG. 2D shows the inflatable member 30 in the inflated position. It is understood that inflating the inflatable member 30 will fix the insertable portion 90 to a passageway or other part of the anatomical body.

In the preferred embodiment illustrated in FIGS. 2C and 2D, the apparatus 100 comprises an electromagnetic shield 45. The electromagnetic shield 45 may be a braided mesh, as is known in the art, to shield the electrical leads 26 from spurious electromagnetic signals. It is understood that the electromagnetic shield 45 is particularly preferable in cases where the power level of the position signal $S_P$ is not great, and therefore even minor spurious electromagnetic fields could adversely affect the position signal $S_P$.

While the inflatable member 30 can be placed in manmade passageways, such as drilled holes into bones, the inflatable member 30 is also well suited for natural occurring passageways in the body, such as arteries, veins and airways. In smaller veins, particularly where the blood flow is not to a crucial part of the body, or alternate blood paths are available, the inflatable member 30 may encompass the entire circumference of the insertable portion 90 as shown in FIGS. 2A, 2B, 2C and 2D. In this case, inflating the inflatable member 30 may occlude the passageway preventing fluid flow through the passageway.

Figure 3A:
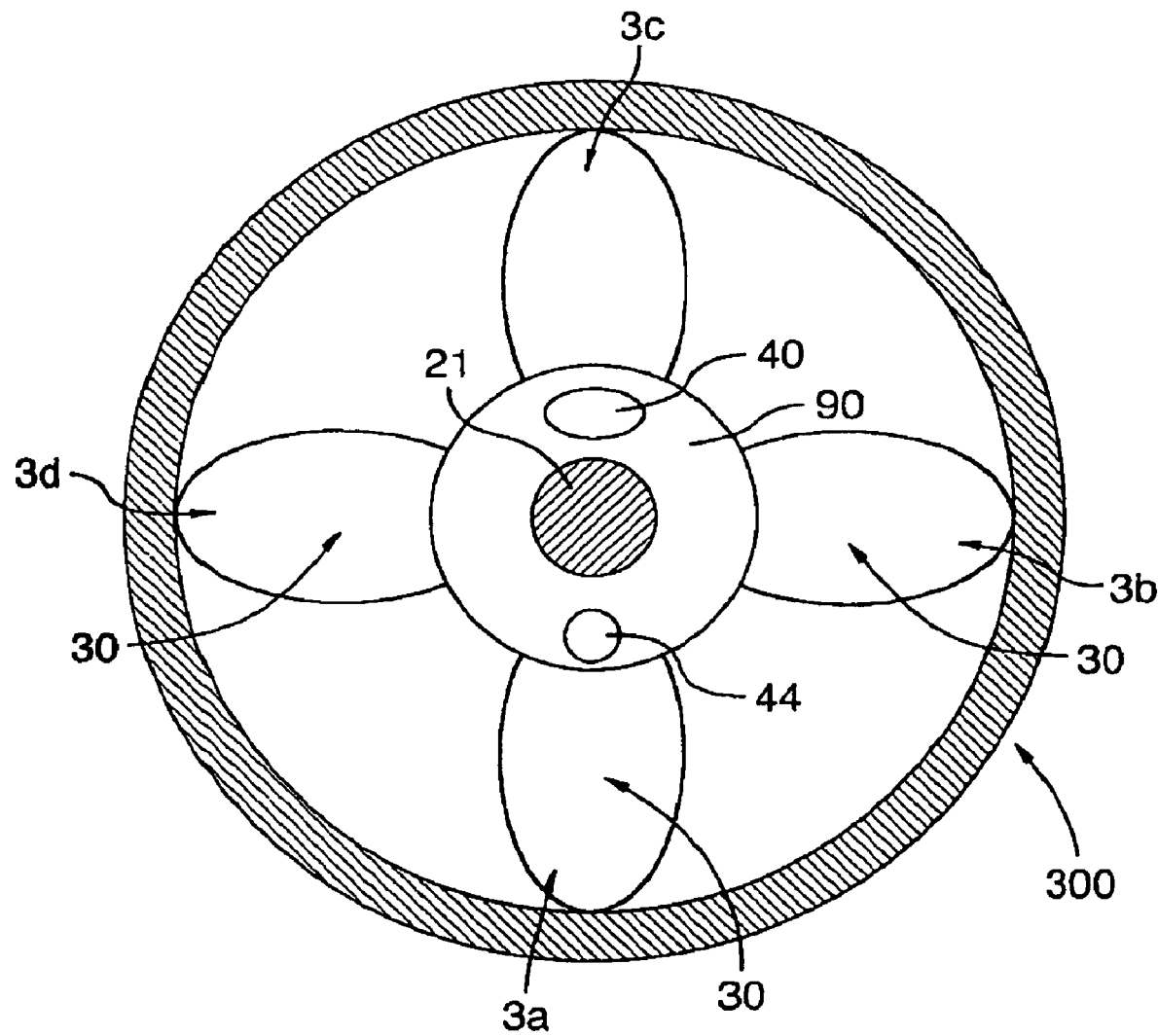
FIG. 3A is a front section view of a catheter having an inflatable member according to a further embodiment of the present invention.

In some cases, however, it is not desirable to completely occlude a passageway. This would be the case, for example, in an airway or main artery. In these cases, it is preferable that the inflatable member 30 comprises at least one lobe portion 3. In the preferred embodiment illustrated in FIG. 3A, the inflatable member 30 comprises four lobe portions 3a, 3b, 3c and 3d, located at 90 degrees with respect to each other and around the insertable portion 90. FIG. 3A illustrates the inflatable member 30 in the inflated configuration, and thereby fixing the insertable portion 90 to a part of the anatomical body, in this case the passageway 300. It is understood that in the deflated configuration, the lobes 3a, 3b, 3c and 3d of the inflatable member 30 would be near the rigid portion 90 in order to permit insertion of the insertable portion 90 into the anatomical body.

It is apparent from FIG. 3A that by utilizing the lobe portions 3a, 3b, 3c, 3d, fluid can still flow around the insertable portion 90 of the apparatus 100, which in this embodiment comprises the catheter 110, and therefore through the passageway 300. In this way, use of lobe portions 3 to fix the insertable portion 90 will not greatly adversely affect the fluid flow in a location of interest. This may be particularly important depending on the pathology of the location of interest and the nature of the passageway 300.

FIG. 3A also shows in cross-section the sensor coil 21 located within the insertable portion 90. FIG. 3A also shows the guidewire path 40 through which the guidewire 60 passes and the inflatable opening 44 through which fluid can pass in order to inflate the inflatable member 30, which in this case comprises the three lobes 3a, 3b, 3c, 3d, attached to a catheter 110 in this embodiment. It is understood that an apparatus 100 other than a catheter 110 could also be used with the inflatable member 30, such as an endoscope (not shown).

Figure 3B:
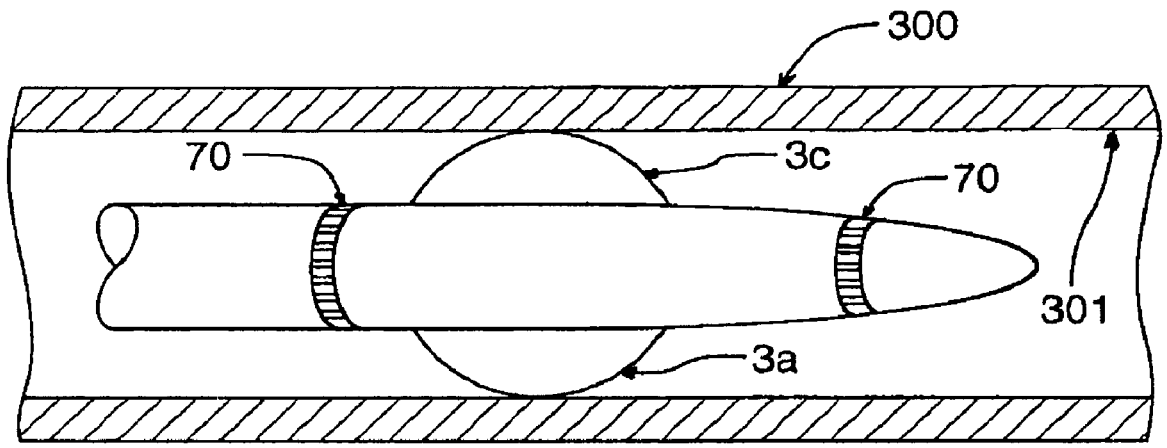
FIG. 3B is a side section view of the catheter shown in FIG. 3A.

FIG. 3B shows a side view of the embodiment illustrated in FIG. 3A. As FIG. 3B is a side view, only lobes 3c and 3a are illustrated. It is understood that lobes 3d and 3b would be entering out of and into the page, respectively. FIG. 3B also shows the fiducial markings 70 at opposed ends of the insertable portion 90.

Figure 3C:
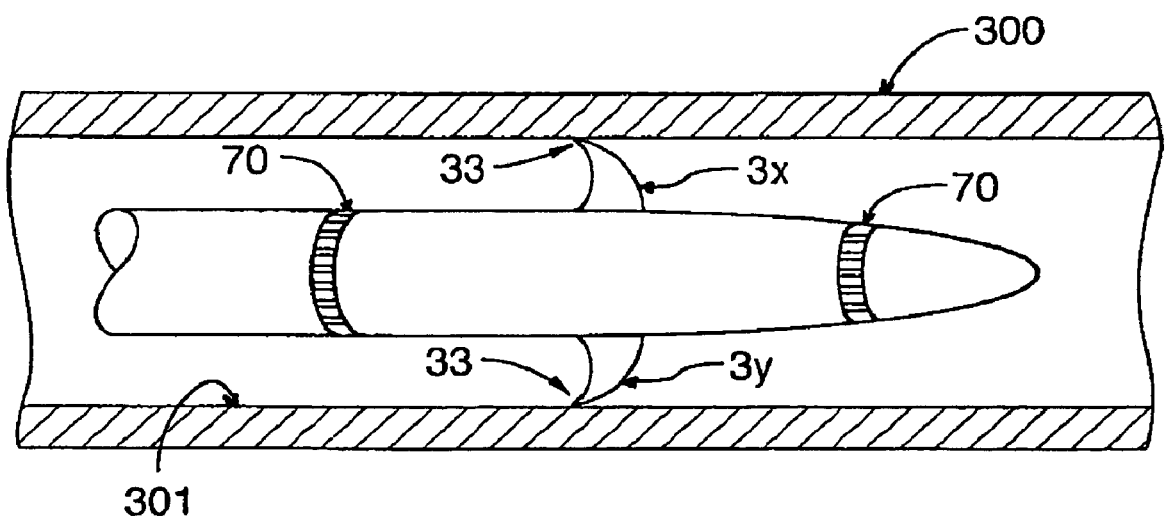
FIG. 3C is a side view of an alternate embodiment of the inflatable member shown in FIG. 3B.

FIG. 3C shows a further embodiment of the present invention where the lobes, in this embodiment identified by reference numerals 3x and 3y, are barbed shaped. The barb shaped lobes 3x and 3y more rigidly secure the insertable portion 90 to the passageway 300. It is understood that while two of the lobe portions 3 are barb shaped lobes 3x, 3y, the insertable portion 90 may also have other lobes 3 which may not be barb shaped, but rather may be shaped similar to lobes 3d and 3b.

In a further preferred embodiment, the barbed shaped lobes 3x, 3y may also have a barbed end 33 for engaging the surface 301 of the passageway 300. The barbed ends 33 may be made of more rigid material in order to permit engaging of the barb shaped lobes 3x, 3y to the surface 301 of the passageway 300. The barbed ends 33 would move towards the insertable portion 90 when the barb shaped lobes 3x, 3y are deflated.

FIGS. 4A and 4B illustrate a further embodiment of the present invention. As shown in FIG. 4A, the catheter 110 comprises a fixing mechanism 28 having a plurality 400 of longitudinally extending fingers 410. The plurality 400 of longitudinally extending fingers 410 is fixed to the rigid portion 90 of the catheter 110 at point 430. The longitudinally extending fingers 410 also comprise a pivoting connection 440, such as a hinge, permitting the longitudinally extending fingers 410 to pivot about point 430.

Each longitudinally extending finger 410 has a gripping element 420 for gripping a surface 301 of the passageway 300 when the insertable portion 90 is near the location of interest. As also illustrated in FIGS. 4A and 4B, the insertable portion 90 has a bead 73 and band 74 as the fiducial markings 70. While the gripping element 420 is shown in FIGS. 4A and 4B as being at the end of the longitudinally extending fingers 410, it is understood that the gripping element 420 could be at any location along the longitudinally extending fingers 410, such as at a bend (not shown) in a mid-portion.

FIG. 4B shows the longitudinally extending fingers 410 in the collapsed configuration where the gripping elements 420 are near the catheter 110. In the collapsed configuration, the insertable portion 90 of the catheter 110 can be more easily inserted into the anatomical body. Once the insertable portion 90 is near the location of interest, the longitudinally extending fingers 410 can be moved to the deployed configuration, shown in FIG. 4A, where the gripping elements 420 engage the surface 301 of the passageway 300. The longitudinally extending fingers 410 may be moved from the collapsed configuration to the deployed configuration in any manner. For instance, the movement may be performed by use of magnetic field acting on the finger 410. In a preferred embodiment, as illustrated in FIGS. 4A and 4B, the fingers 451 are moved from the collapsed configuration to the deployed configuration by mechanically moving the supports 450 for each of the longitudinally extending fingers 410. The supports 450 can be extended by signals received in any manner, including mechanically, electrically, pneumatically, hydraulically or through the use of light signals transmitted through fibre optics.

It is apparent from FIG. 4A that when the longitudinally extending fingers 410 are in the deployed configuration, fluid can still flow around the catheter 110, and therefore through the passageway 300. In other words, deployment of the longitudinally extending fingers 410 does not occlude the passageway 300. Once the procedure is completed, the fingers 410 can be moved from the deployed configuration to the collapsed configuration in the same manner in which they were deployed.

Figure 5:
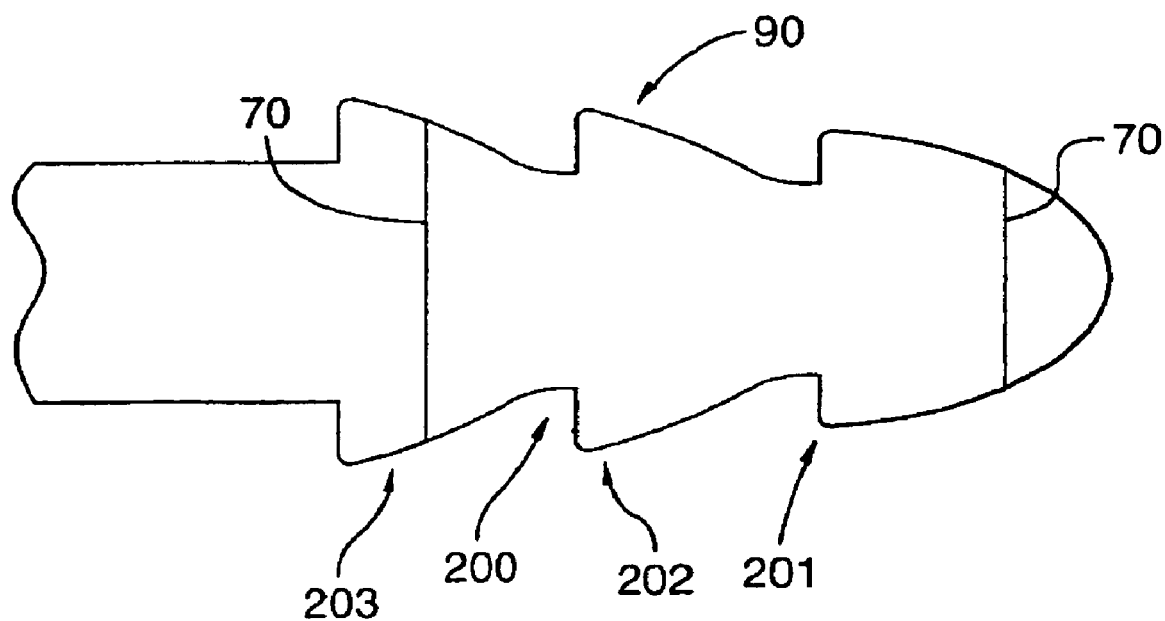
FIG. 5 shows a side view of the rigid portion of the catheter according to a further embodiment of the present invention.

FIG. 5 shows an alternate embodiment where the fixing mechanism 28 comprises barbs 200. The embodiment illustrated in FIG. 2E has three barbs 201, 202, 203, but it is understood that even one barb 201 may be sufficient. The barbs 200 form part of the insertable portion 90 that holds the position sensor 20. In this embodiment, the barbs 200 form an integral part of the insertable portion 90. Fiducial markings 70 are shown on barbs 201, 203, which are near opposed ends of the insertable portion 90.

Fixing mechanisms 28, such as the barbs 200, could be used in association with different parts of the anatomical body, and in particular bone. For example, a manmade passageway, such as a drilled hole, could be made in a bone, such as a spine segment, the skull or the femur. The insertable portion 90 could then be inserted into the drilled hole such that at least one of the barbs 200 fixes the insertable portion 90 to the bone. Depending on whether the procedure would need to be repeated in the near future, and the size of the insertable portion 90, it may be preferable to maintain the insertable portion 90 within the bone for an extended period of time.

Figure 6A:
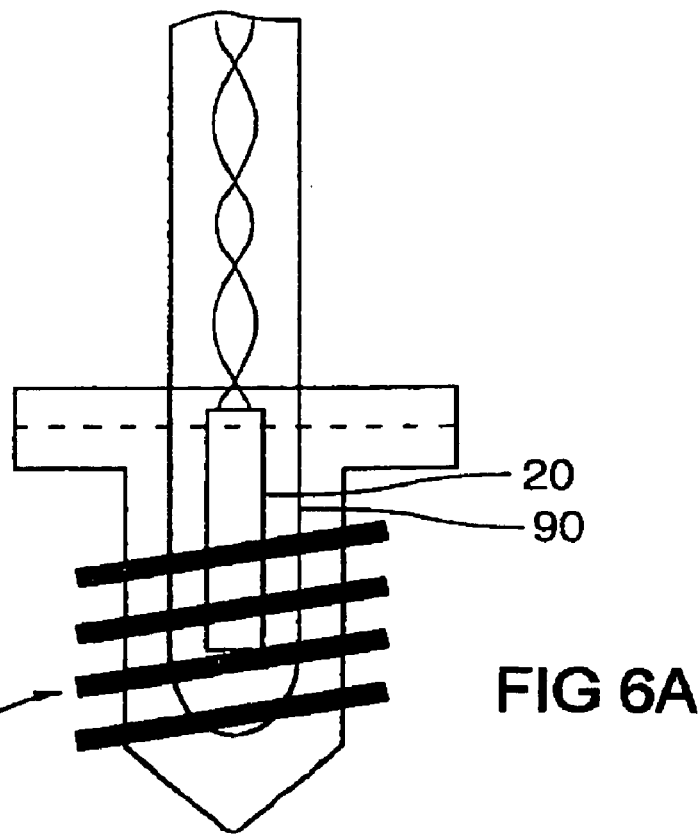
FIG. 6A shows a detailed view of the catheter according to a further embodiment of the present invention.
Figure 6B:
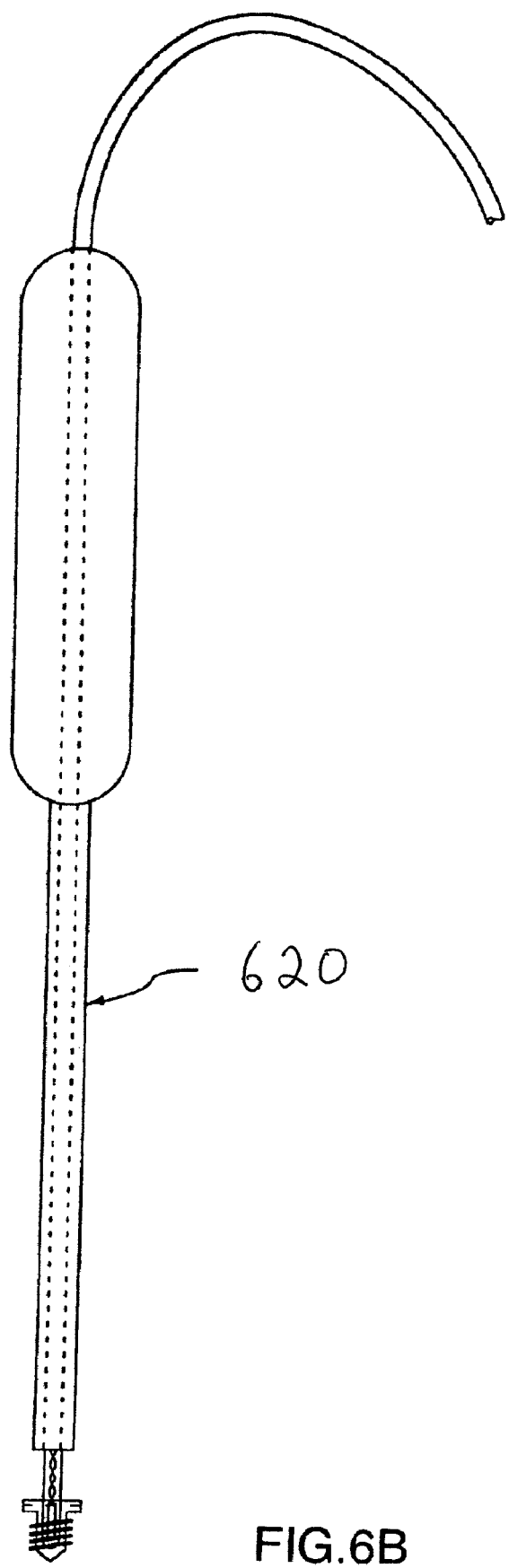
FIG. 6B shows a side view of the catheter shown in FIG. 6A attached to a cannulated screwdriver.

In a further embodiment, illustrated in FIGS. 6A and 6B, the insertable portion 90 comprises a screw structure 610. The screw structure 610 is designed to screw the insertable portion 90 into a passageway within the anatomical body. Preferably, such a passageway would be made within bone so that the screw structure 610 can grip into the edges of the passageway and draw the insertable portion 90 within the passageway to rigidly fix it therein. As shown in FIG. 6A, the position sensor 20 is contained within the insertable portion 90. FIG. 6B illustrates a cannulated screwdriver 620 which can be used to rotate the insertable portion 90 so that the screw structure 610 can engage the edges of the passageway to rigidly fix the insertable portion 90 therein. In this embodiment, it is particularly preferable to have an insertable portion 90 to withstand the torque forces encountered when the cannulated screwdriver 620 rotates the screw structure 610.

It is understood that the present invention also contemplates a method for registering a position sensor 20 to an anatomical body as described above. In particular, the present invention relates to a method of fixing a position sensor 20 to an insertable portion 90 of a catheter 110, the insertable portion 90 having fiducial markings 70 as described above. The method also comprises inserting the insertable portion 90 of the catheter 110 to the location of interest in the anatomical body. The fiducial markings 70 are then detected on the insertable portion 90 of the catheter 110 to facilitate registration of the position sensor 20 in the insertable portion 90 to the anatomical body.

As described above, it is understood that detecting the registration step includes detecting the fiducial markings 70 on the insertable portion 90. In the case where an imaging modality is used, the fiducial markings 70 would be detected on the insertable portion 90 by viewing the image obtained through the image modality. It is understood that other types of methods and means could be used to detect the fiducial markings 70 on the insertable portion 90 once the insertable portion 90 has been inserted to the location of interest.

The position of the position sensor 20 in the frame of reference can then be determined using the system 110. Having obtained a determined position of the position sensor 20 in the frame of reference using the system 10, the position sensor 20 can then be registered to the anatomical body by correlating the detected fiducial markings 70 to the determined position of the position sensor 20. In this way, the position sensor 20 can be registered to the anatomical body and movement of the position sensor 20 in the frame of reference can then be used to track movement of the location of interest in the anatomical body.

Figure 7:
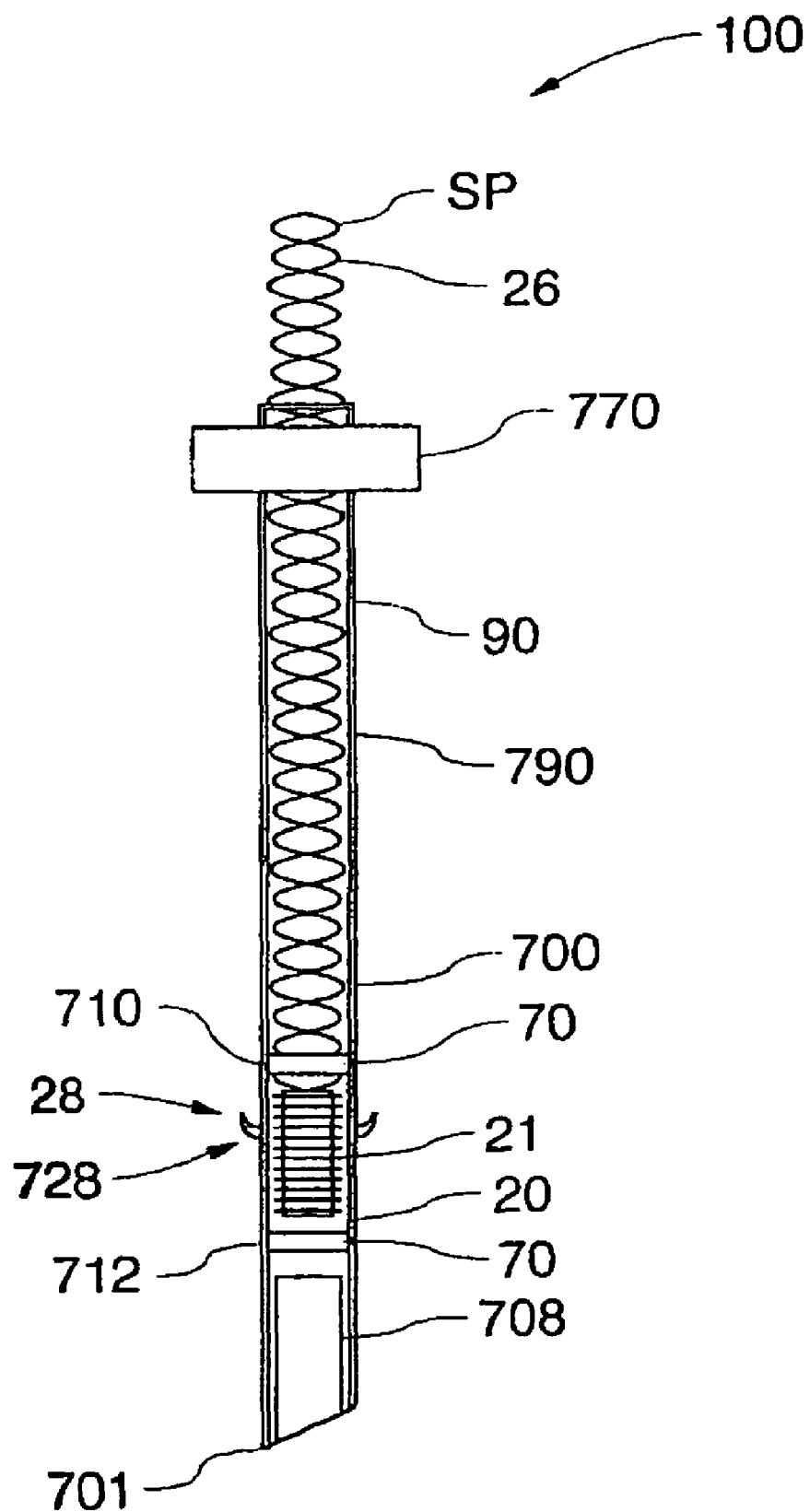
FIG. 7 illustrates an insertable portion in the form of a stylette insertable in a needle, according to a further embodiment of the present invention.
Figure 8A:
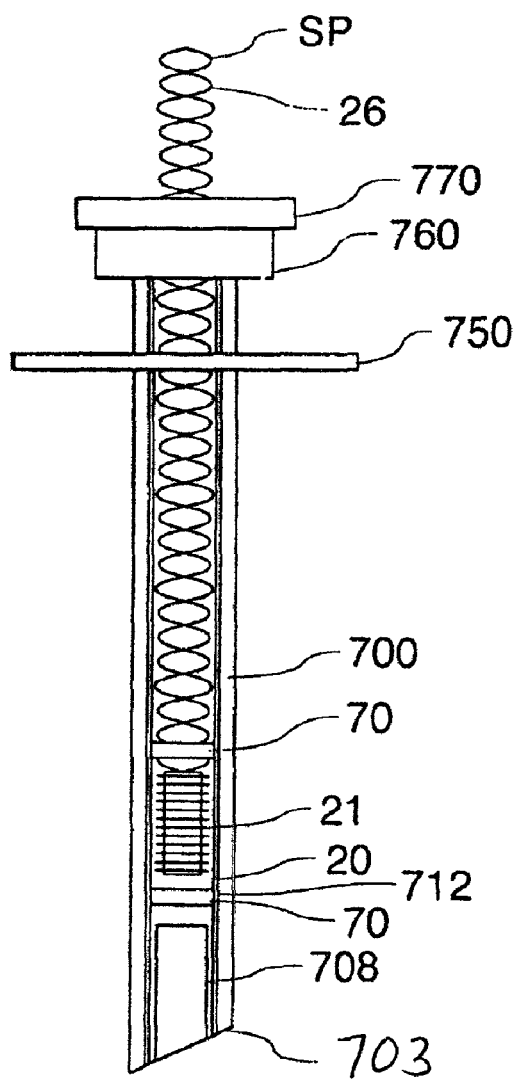
FIGS. 8a and 8b illustrates an apparatus comprising a needle and an insertable portion in the form of a stylette releasably fixed into the needle according to a further embodiment of the present invention.
Figure 8B:
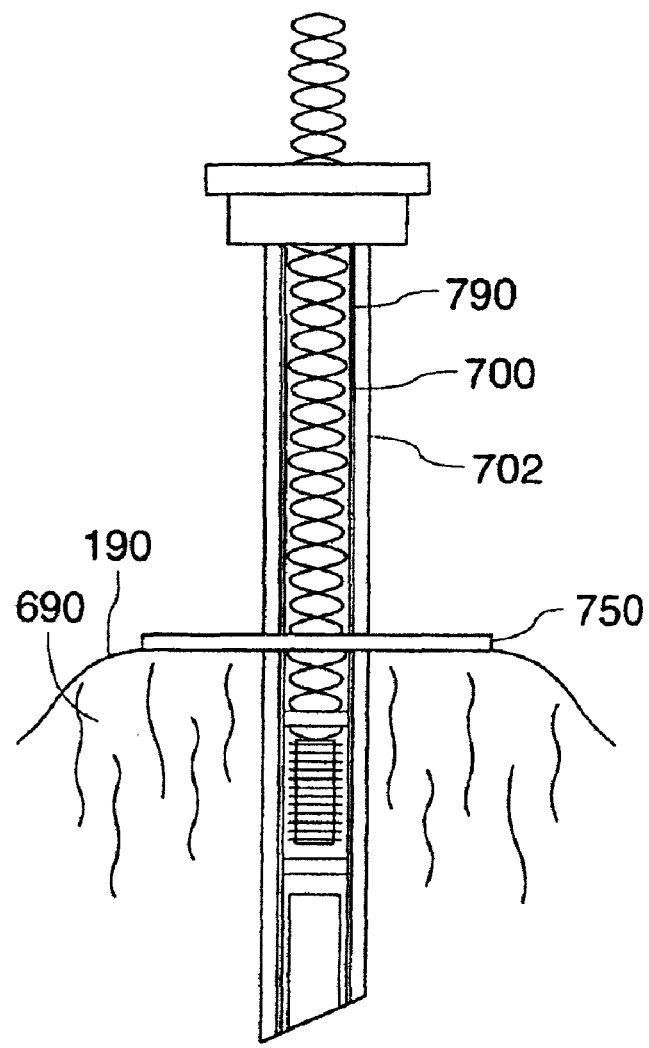

FIG. 7 shows a further embodiment of the present invention where the insertable portion 90 comprises a stylette 790 which can be inserted into a needle 702, as shown in FIGS. 8a and 8b. The stylette 790 comprises a hollow stylette 700 as is known in the art. The hollow stylette 700 holds a position sensor 20 comprising a sensor coil 21, as discussed above. The sensor coil 21 is connected to sensor leads 26 for transmitting the position signal $S_P$ from the sensor coil 21 of the position sensor 20 to the sensor interface unit 18 the control unit 12 and the host computer 16, similar to the manner described above. The position signals $S_P$ generated by the sensor coil 21 is indicative of both the position and orientation of the position sensor 20 held within the hollow stylette 700.

The stylette 790 also comprises fiducial markings 70. The fiducial markings 70 are detectable by an imaging modality when the stylette 790 is inserted into the anatomical body. The fiducial markings 70 can be any markings that permit the position and orientation of the stylette 790 to be determined from images obtained by imaging modality, as discussed above. In one preferred embodiment, as shown in FIG. 7, the fiducial markings comprise two bands 710, 712.

The stylette 790 also comprises a stylette hub 770. The stylette hub 770 on the hollow stylette 700 mates with the corresponding needle hub 760 on the needle 702. In this way the hollow stylette 700 can be releasably fixed to the needle 702. This also ensures that the orientations of the hollow stylette 700 and the needle 702 are consistent.

This is the case in part, because the tip 701 of the stylette 790 is cut in a manor consistent with a tip 703 of the needle 702 and therefore they are preferably oriented together.

Generally, a stylette is made of a wire (not shown) that simply blocks the central cavity of needle 702. But because this stylette 790 comprises a hollow stylette 700, a stylette plug 708 is preferably used at the tip 703 of the needle 702 to prevent entry of tissue 690 into the hollow stylette 700.

FIG. 8a shows the stylette 790 releasably fixed within the needle 702. As shown in FIG. 8a, a sliding washer 750 is present on the needle 702, for contacting the tissue 690 of the anatomical body 190, as shown in FIG. 8b. Accordingly, as shown in FIGS. 8a and 8b, the stylette hub 770 is initially mated with the needle hub 760 to releasably fix the needle 702 to the hollow stylette 700 and to ensure that their orientations are consistent. The needle 702 can then be used to insert the stylette 790 into the anatomical body 190. At this time, the sliding washer 750 may be slid down the needle 702 to contact the tissue 690 of the anatomical body 190 as shown in FIG. 8b.

At this time, an imaging modality may be used to detect the fiducial markings 70 on the stylette 790. In this way, the position sensor 20 can be registered to the anatomical body 190 by correlating the fiducial markings 70 detected by the image modality to the determined position of the position sensor 20 in the frame of reference, as discussed above.

Accordingly, this is an additional embodiment of the present invention where the apparatus 100 comprises a stylette 790 which can be inserted into the anatomical body 190 using the needle 702. In this embodiment, the position sensor 20 can be used to ensure that the needle 702 has been inserted into the location of interest in the anatomical body 190. At that time, the stylette 790 may be removed as shown in FIG. 8c and the needle 702 used to deliver a drug, therapeutic agent, or monitor activity at the location of interest. A biopsy needle (not shown) could also be inserted through the needle 702 shown in FIG. 8c so that the biopsy needle protrudes from the tip of the needle 702 to take a biopsy from the tissue 690, such as parts of organs, tumours or body fluids.

It is understood that once the needle 702 is in the location of interest the stylette 790 is no longer required for guidance and may be removed so that the needle 702 can be used in a procedure. However, if after the procedure the needle 702 is required to be moved again, or the movement of the anatomical body 190 around the needle 702 is to be tracked, the stylette 790 may be reinserted into the needle 702 for a dynamic or partial dynamic reference of the needle 702 in the anatomical body 190. It is understood that the stylette 790 may need to be reregistered if it has been reinserted into the needle 702.

Figure 10:
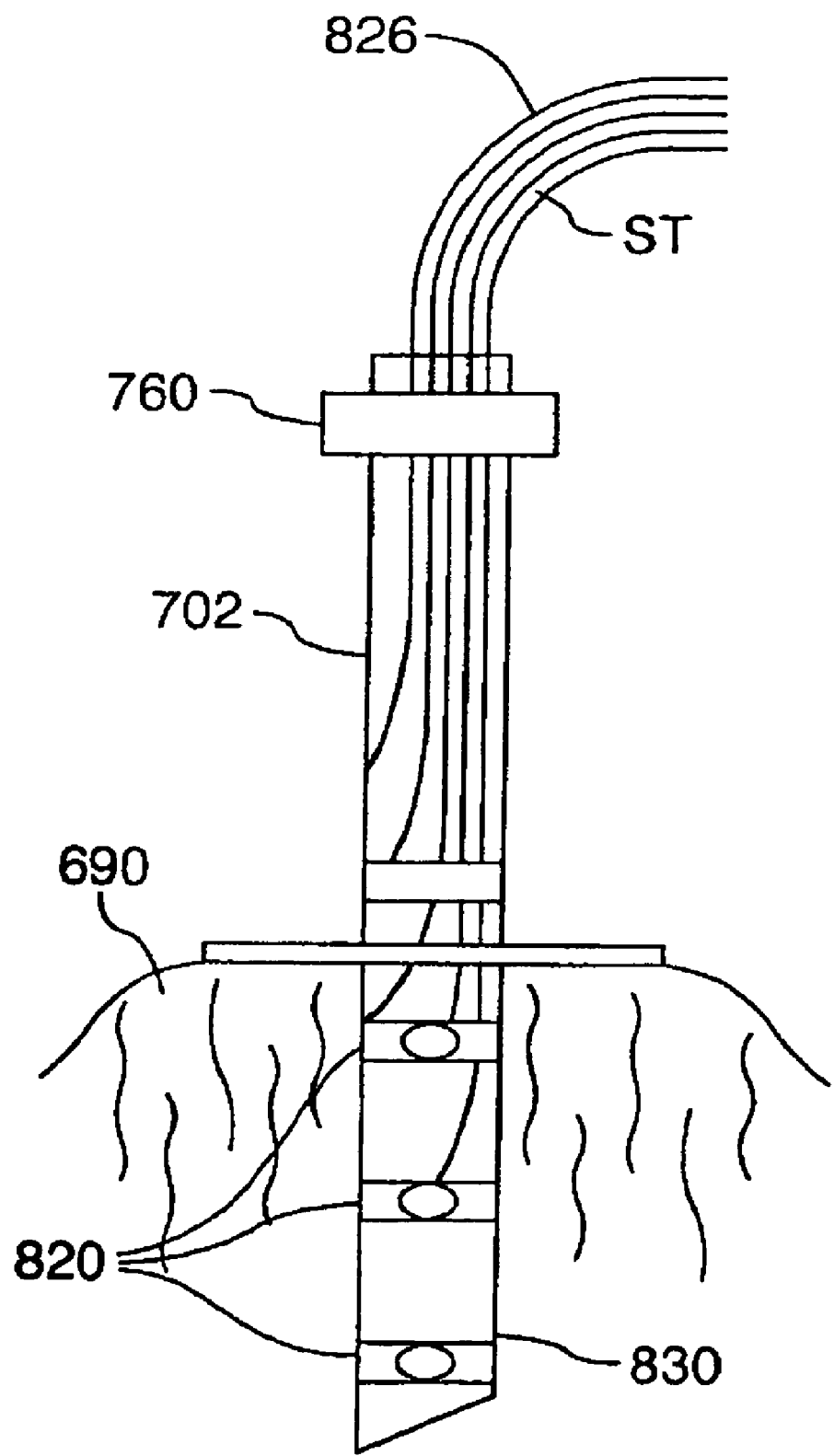
FIG. 10 illustrates a needle with therapy or sensor zones according to a further embodiment of the present invention.

In a further embodiment, as shown in FIG. 10, the needle 702 may contain on a surface 830 having therapy or sensor zones 820. The therapy or sensor zones 820 can likewise be inserted to a location of interest in the anatomical body 190 using a position sensor 20 in the stylette 790. In FIG. 10, a stylette 790 has been shown removed from the needle 702, although this need not necessarily be done. Rather, the stylette 790 has been shown removed in FIG. 10 for ease of illustration.

Once the needle 702 is in the location of interest or near the location of interest, the therapy or sensor zones 820 can be activated. In other words, the therapy or sensor zones 820 can either provide a therapy to the location of interest, or, sense activities in the location of interest. For instance, the therapy or sensor zones 820 located on the surface 830 may be capable of measuring a second unrelated parameter such as electrical activity, pressure, temperature, radiation or any other type of parameter including content or concentration of other types of substances. The therapy or sensor zones 820 could also be used to deliver a therapeutic substance. Such therapeutic substances can include energy in the form of heat, electrical signals, radio frequency (RF) energy, high frequency sound, ultrasound, microwave, x-rays, particle beams laser energy through a fibre optic cable, or other types of radiation. The therapy or sensor zones 820 could also be used to scan the inside of blood vessels or other anatomical features, such by using magnetic resonance. In a further embodiment, the therapy or sensor zones 820 may facilitate delivering a therapy such as a drug or radioactive seed that can be inserted into the needle 702 if the stylette 790 has been removed.

As illustrated in FIG. 10, the stylette 790 comprises therapy/sensor leads 826 for transmitting the therapeutic signals $S_T$ from the therapy or sensor zones 820 indicative of the sensed second parameter as discussed above. The therapy/sensor leads 826 may also transmit control signals $S_C$ to control the therapy/sensor zones 820.

It is understood that the stylette 790 preferably holds the position sensor 20 within the needle 702 such that the position and orientation of the fiducial markings 70 with respect to the insertable portion 90 remains substantially constant. It is understood that because the needle 702 is generally more rigid than the hollow stylette 700, the rigidity of the needle 702 will assist in maintaining the position and orientation of the fiducial markings 70 with respect to stylette 790 substantially constant.

FIG. 9 shows a further embodiment of the present invention comprising a secondary stylette 704 for holding secondary sensor 705. In this embodiment, the secondary stylette 704 contains a secondary sensor 705 and the secondary stylette leads 729 transmit the sensor signals $S_S$ generated by the secondary sensor 705. Accordingly, in this embodiment, the apparatus 100 comprises a needle 702 and a hollow stylette 700 releasably fixed within the needle 702, as well as the secondary stylette 704. The stylette 790 is initially releasably fixed within the needle 702. Once the needle 702 has been inserted to or near a location of interest, the stylette 790 can be removed and the secondary stylette 704 inserted into the needle 702. The secondary sensor 705 of the secondary stylette 704 can then sense a secondary parameter, likely other than position, and transmit sensory signals $S_S$ through the secondary leads 729 to the sensor interface unit 18 or another interface unit (not shown).

Figure 11:
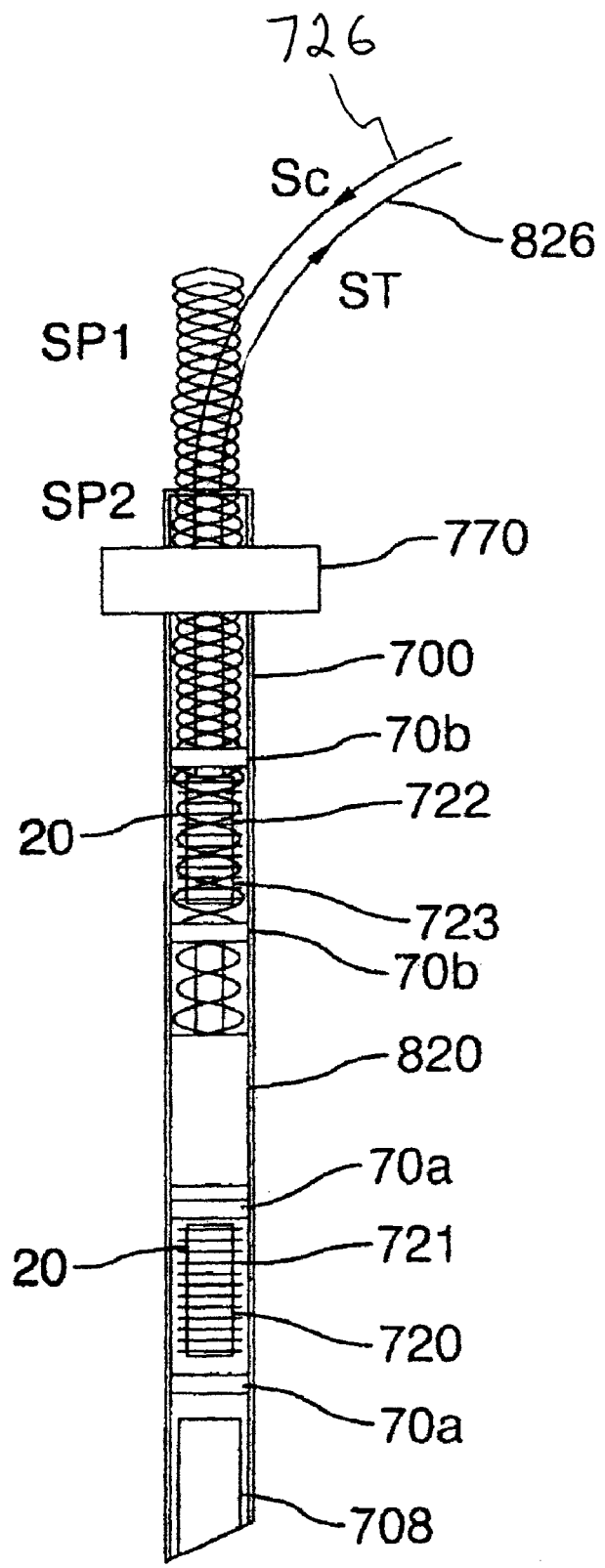
FIG. 11 illustrates an embodiment of the present invention having two position sensors longitudinally displaced according to a further embodiment of the present invention.

FIG. 11 illustrates an embodiment where the position sensor 20 of the stylette 790 comprises a first position sensor 720 and a second position sensor 722. The first position sensor 720 has a first sensor coil 721 for generating a position signal $S_{P1}$ indicative of the position of the first position sensor 720 in the fixed frame of reference. Likewise, the second position sensor 722 has a second sensor coil 723 for generating a second position signal $S_{P2}$ indicative of the position of the second position sensor 722 in the frame of reference. Preferably, the first position sensor 720 is longitudinally displaced from the second position sensor 722. This is the case, in part, so that the first position sensor 720 can be displaced from the second position sensor 722. Because the stylette 790 is designed to fit within the needle 702, the position sensors 720, 722 can best be displaced by displacing them longitudinally axis of the stylette 790. Also, in a preferred embodiment, a secondary sensor or therapy device 820 is longitudinally located between the first position sensor 720 and the second position sensor 722. This permits the position of the secondary sensor or therapy device 820 to be more clearly determined, as it is located between the two position sensors 720, 722.

Because the position sensors 720, 722 are displaced to such an extent, it is generally preferred that each of the position sensors 720, 722 have their own fiducial markings 70a and 70b. The fiducial markings 70a, 70b operate in a manner as described above, to facilitate registration of the position sensors 720, 722 in the anatomical body 190 by correlating the fiducial markings 70a, 70b detected by the imaging modality to the determined position of the position sensors 720, 722 irrespectively in the frame of reference. As discussed above, the stylette 790 may bend when the needle 702 has been removed. Because of this, it is generally necessary to have fiducial markings 70a, 70b associated with each position sensor 720, 722, to accommodate for any bending by the stylette 790.

The position signals $S_{P1}$, $S_{P2}$ from the first and second position sensors, 720, 722 travel along the sensor leads 826 to the sensor interface unit 18, as discussed above. The stylette 790 illustrated in FIG. 11 also comprises further leads. The further leads travel from the secondary sensor or therapy device 820 to an interface unit, which may also be the sensor interface unit 18, for analysing the signals $S_T$ from the secondary sensor or therapy device 820. Alternatively, the therapy signals $S_T$ may enter a separate interface device (not shown). In addition, control signals $S_C$ 726 may be sent to the secondary sensor or therapy device 820 to control its operation.

It may be desired to have the stylette 790 fixed to the anatomical body 190 at or near a location of interest. This could be the case, for example, if the position sensor 20 is to dynamically reference the tissue 690. In a preferred embodiment, the stylette 790 comprises a fixing mechanism 28. The fixing mechanism 28 can comprise a simple mechanical element such as barbs 728 illustrated in FIG. 7. The barbs 728 can be used, for example, to fix the stylette 790 in the tissue 690 such as the liver or muscle.

Figure 12:
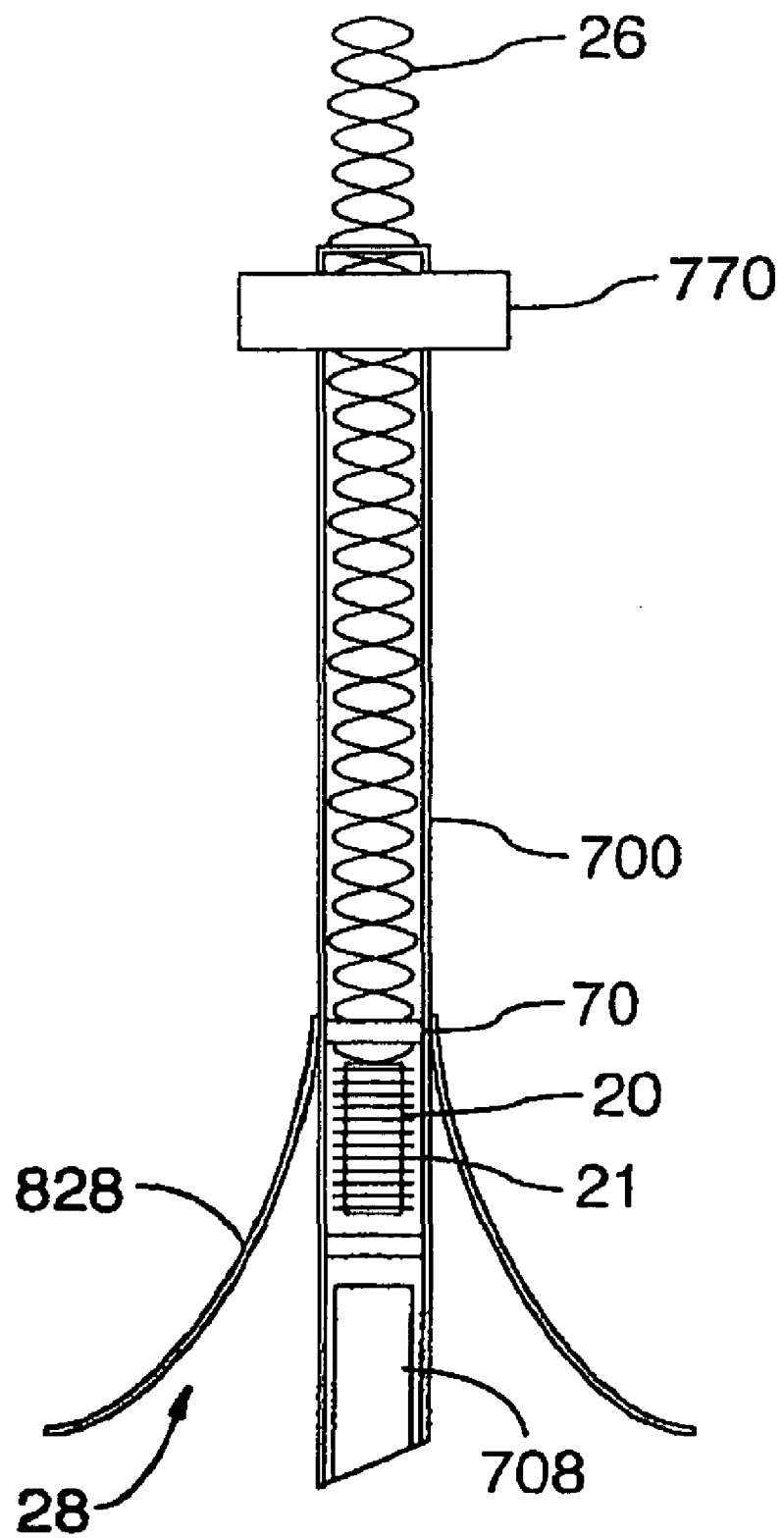
FIG. 12 illustrates an insertable portion for insertion in a needle with the insertable portion having a fixing mechanism.

In a further preferred embodiment, the fixing mechanism 28 comprises deployable stabilization members 828 as illustrated in FIG. 12. The deployable stabilization members 828 are preferably located near the position sensor coil 21 to fix the position sensor 20 to the anatomical body 190 at or near a location of interest.

FIGS. 13a, 13b and 13c illustrate operation of the deployable stabilization members 828. As illustrated in FIG. 13a, when the stylette 790 is releasably fixed within the needle 702, the deployable stabilization members 828 are in a collapsed configuration. In FIG. 13b, the needle 702 is near or at the location of interest and the stylette hub 770 can be removed thereby releasing the needle 702 from the stylette 790 and permitting the needle 702 to slide out. Removing the needle 702 causes the deployable stabilization members 828 to move to a deployed configuration, as shown in FIG. 13c. In the deployed configuration, the stylette 790 is releasably fixed to the anatomical body 190 near or at the location of interest. The position sensor 20 can now sense the position of the location of interest. Once the procedure is completed, the stylette 790 can be removed by pulling the stylette 790 from the anatomical body 190.

Figure 14D:
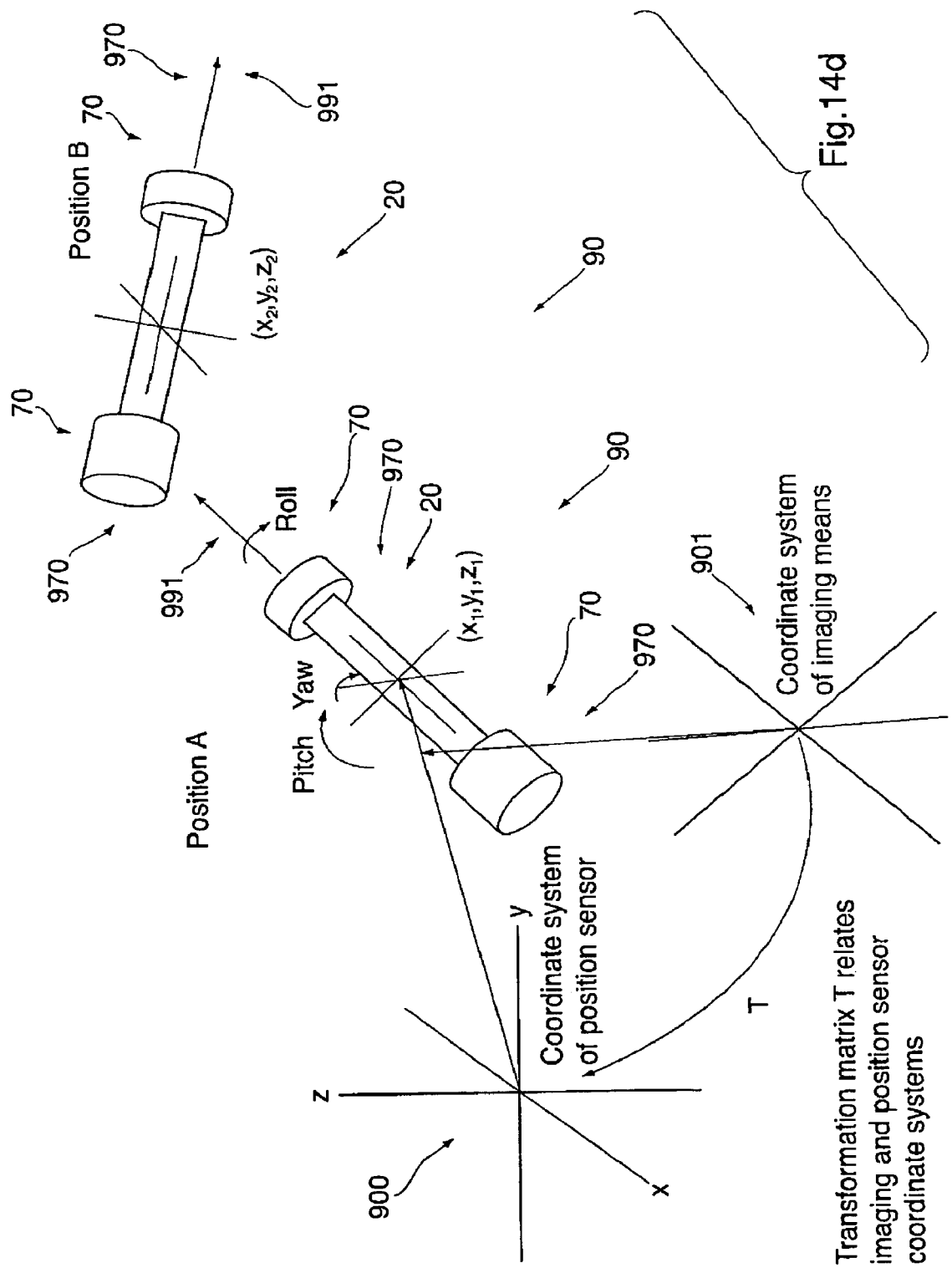

FIGS. 14a, 14b, 14c and 14d illustrate the registration procedure according to one preferred embodiment of the present invention. As illustrated in FIG. 14a, a reference coordinate system 900 is provided in the laboratory frame of reference. For ease of reference, the laboratory reference coordinate system 900 will also correspond to the field generator 14 coordinate system. As also illustrated in FIG. 14a, there is an insertable portion 20 at position A and either another insertable portion 20 or the same insertable portion 20 at a position B. As illustrated in FIG. 14a, the insertable portions 20 at positions A and B will have coordinates $x_1$, $y_1$ and $z_1$ and $x_2$, $y_2$ and $z_2$ in the reference coordinate system 900.

FIG. 14b illustrates the coordinate measurements of points $x_1$, $y_1$, $z_1$ and $x_2$, $y_2$ and $z_2$ of positions A and B, respectively using the position sensor 20. That is, FIG. 14b illustrates that the coordinate measuring system including the position sensor 20 sees the location and orientation of the position sensor in its internal coordinate system 900. These would be the measurements made for instance by the field generator 14. FIG. 14b also illustrates the coordinate system of the imaging means or modality 901. As shown in FIG. 14a, the positions A and B are only determined in the coordinate system 900 of the field detector system including the field generator 14 and the position sensor 90 because the position sensor 90 can only be detected by the field generator 14. In a preferred embodiment, the position sensor 20 may also be able to determine the orientations along two axes shown as pitch and yaw in FIG. 14b. More preferably, the position sensor 20 will also be able to determine the orientation along the roll axis, although most currently available position sensors cannot measure the orientation along one axis, and generally the roll axis.

FIG. 14c illustrates the images of the fiducial marking 70 as determined using the imaging modality. That is, FIG. 14c illustrates that the imaging system sees in the image the location of the position sensor in the internal image coordinate system 901. In this way, the coordinates at position A and B are determined with respect to the coordinate system 901 of the imaging means. It is also noticed that, in addition to the six degrees of position and orientation, the direction illustrated generally by the arrow and reference numeral 991, is also determined. This is determined in the embodiment illustrated in FIG. 14c in part because the fiducial markings 70 are asymmetrical fiducial markings 970 which can be differentiated in order to unambiguously determine the direction 991 in the image coordinate system 901.

FIG. 14d illustrates determination of the transformation matrix T by correlating the positions A, B as determined from the fiducial markings 70 detected by the imaging modality in the coordinate system of the imaging means 901 to the position of the position sensors 20 and the coordinate system of the field generator 900. In this way, the transformation matrix T can be determined and used to correctly map measurements of the movement of the position sensors 20 and the orientation of the position sensors 20 to images obtained through the imaging modality. Accordingly, once the transformation matrix T has been obtained, the coordinate system 900 of the field generator 14 has been registered to the coordinate system of the imaging means 901 permitting image guided surgery to then take place.

As illustrated in FIGS. 14c and 14d, the position and orientation, illustrated by x, y, z and pitch, yaw, roll, may be determined in order to facilitate determination of the transformation matrix T and registration of the system. It is apparent that the direction 991 determined from the fiducial markings 70 can also be of assistance to avoid any ambiguity. For instance, in cases where the fiducial markings 70 are symmetrical about all of the axes, ambiguity can arise in the imaging modality, illustrated in FIG. 14c, because it would not be easily determinable which fiducial markings 70 is which. To overcome this, in a preferred embodiment, as illustrated in FIGS. 14c and 14d, the fiducial markings 70 comprise asymmetrical fiducial markings 970 which are asymmetrical about at least one axis of the insertable portion 90.

FIGS. 15a and 15b also illustrate having asymmetrical fiducial markings or bands 1 and 2 971, 972 which are asymmetrical about at least one axis, this being the y axis as illustrated in FIGS. 15a and 15b. The asymmetrical fiducial markings 970 facilitate unambiguous registration by assisting in determining the direction 991 of the sensor 20.

This is further illustrated in FIGS. 16a and 16b which illustrate the image which would be obtained of the fiducial markings 971, 972 using the image modality. As illustrated in FIGS. 16a, 16b, the asymmetrical fiducial markings are asymmetrical about at least the y axis. This facilitates determination of the direction 991. Had the fiducial markings been symmetrical about the y axis (not shown), the direction 991 could not be unambiguously determined. It is also apparent that the fiducial markings 971, 972 are symmetrical about the x-axis. In this way, orientation along the x-axis cannot be easily determined. However, as indicated above, many position sensors 20 cannot determine orientation along one axis, such as the roll axis. In this case, preferably the x-axis, about which the fiducial markings 971, 972 are symmetrical, coincide with the x-axis about which the markings 971, 972 are symmetrical so that lack of determination of orientation along this axis is not significant.

FIGS. 17a, 17b and 17c illustrate further preferred embodiments of the present invention where the rigid portion 990 comprises a mantle 999. The mantle 999 is manufactured of a material which can be imaged in the imaging modality. The mantle 999 may constitute the rigid portion 990 or alternatively may be contained within an outer portion 981 or may be encased or contained within material not imaged in the imaging material. The mantle 999 may be a continuum having a continuous 2 or 3 dimensional shape, or, may be two or more discrete shapes. In this way, the mantle 999 may be considered as comprising fiducial markings 70 along the entire surface. The mantle 999 is rigidly attached by the rigid attachment 921 to the position sensor 920. The mantle 999 is shown as being asymmetric about at least one axis, in this case the y axis, as also illustrated in the profile shown in FIG. 17a. For example, the mantle 999 is axially symmetric but not symmetric in reflection. In this way, the direction 991 of the mantle 999, as well as the direction of the sensor 920 may be unambiguously determined.

By way of contrast, FIGS. 18a, 18b and 18c illustrate a further embodiment of a mantle 1000 rigidly attached to a sensor 920. The mantle 1000 shown in FIGS. 18a and 18c can also be imaged by an imaging modality. However, the mantle 1000 is actually symmetric along all three axes as illustrated in FIGS. 18a, 18b and 18c and in this case, it is not possible to unambiguously determine the direction using mantle 991. For example, the mantle 1000 is both axially symmetric and symmetric in reflection.

FIGS. 19a and 19b show a further embodiment of the present invention having a mantle 1001 which is completely asymmetric. In other words, the mantle 1001 is asymmetric along all three axes. This further facilitates unambiguous registration of the sensor 920 because the direction 991 can be unambiguously determined similar to the mantle 999. Furthermore, because the mantle 1001 is completely asymmetrical, and has no plane of reflective symmetry, the mantle 1001 can be used to determine the position of the insertable portion to facilitate unambiguous registration. Because the mantle 1001 has completely asymmetrical shape, it is well suited to be used with position sensors 20 which measure position and orientation in six degrees of freedom, namely x, y, z and pitch, yaw and roll. Accordingly, having fiducial markings on a mantle which comprises as a whole fiducial markings that is axially asymmetrical on at least one axis, facilitates unambiguous registration by assisting in determining the position (x,y,z) and orientation, (yaw, pitch, roll) and direction 991 of the position sensor 920 in the imaging modality.

It is understood that the present device can be used in any anatomical body. For instance, the device 100 can be used on a living human body, as well as a cadaver, such as during an autopsy. Furthermore, the device 100 may be used in non-human anatomical bodies, such as in veterinary use on animals.

It is also understood that the position sensor 20 may be inserted for any reason. For example, the position sensor 20 may be inserted to assist in treatment, diagnosis or monitoring. This is illustrated, for example, at least in FIG. 11 discussed above.

While the present invention has been described in terms of a position sensor 20 comprising a particular type of sensor element, namely the magnetic sensor coil 21, it is understood that the present invention is not limited to this type of sensor. Rather, any type of position sensor, which can sense movement in at least some degrees of freedom, can be used. In particular, fibre optic position sensors, which sense changes in light, could also be used. Furthermore, while the present invention has been described in terms of a magnetic sensor coil 21 connected to electrical leads 26, it is understood that the electrical leads 26 may not be required. For instance, if a fibre optic position sensor 20 is utilized, electrical leads 26 may be replaced by fibre optic cables (not shown). In this case, the electromagnetic shielding 45 may not be needed. It is further understood that the present invention is not limited to position sensors 20 which require an electrical lead 26 or fibre optic (not shown) to transmit the position signals $S_P$ indicative of the movement of the position sensor 20. Rather, the position signals $S_P$ may be transmitted wirelessly directly from the position sensor 20 to a position sensor receiver (not shown) in the frame of reference.

It is also understood that reference has been made to placing the insertable portion 90 near the location of interest and at the location of interest. It is understood that, in this context, near the location of interest also includes at the location of interest, and, how near the position sensor 20 can be placed to the location of interest would change with each situation and depend on the pathology and part of the anatomical body 190 which is in the location of interest. For instance, if a location of interest comprising an organ such as the kidney, position sensor 20 may easily be placed at the location of interest by being placed within passageways 300, such as veins, within the kidney. Conversely, if the location of interest comprises the spinal cord, the spinal cord may be tracked by placing position sensors in spine segments near the spinal cord. Accordingly, it is understood that both "near the location of interest" and "at the location of interest" refer to placing the insertable portion 90 in a location which can best track the location of interest in the anatomical body 190 for the procedure being performed.

It is understood that the insertable portion 90 is rigid to the extent required to keep the position sensor 20 in a known position and orientation with respect to the fiducial markings 70 during the registration procedure. In other words, if the position sensor 20 can be flexible, so that it can be bent and still operate, then the insertable portion 90 can be more flexible. Accordingly, the insertable portion 90 is as rigid as necessary for the position sensor 20 to operate. Furthermore, it is contemplated that the insertable portion 90 could be rigid for a predetermined period of time, such as during registration, and could be more flexible at other times, such as by removing a removable rigid member (not shown) temporarily forming parts of the insertable portion 90.

It is also understood that while the invention has disclosed a number of different fixing mechanisms 28 for fixing the insertable portion 90 containing a position sensor 20, the fixing mechanisms 28 are not limited to this embodiment. Rather, the fixing mechanisms 28 could be used whether or not the catheter 110 contains a position sensor 20, and regardless of the use of the catheter 110.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments that are functional, electrical or mechanical equivalents of the specific embodiments and features that have been described and illustrated herein.

The embodiments of the invention in which an exclusive property or privilege is claimed are defined as follows:

1. An apparatus insertable into an anatomical body, said apparatus comprising:
   an insertable portion holding a position sensor that can transmit a signal indicative of its position in a frame of reference;
   fiducial markings on the insertable portion, said fiducial markings being detectable by an imaging modality when the insertable portion is inserted in the anatomical body and permitting the position and orientation of the insertable portion to be determined, said insertable portion substantially rigidly holding the position sensor at a known spatial position with respect to the fiducial markings;
   wherein the fiducial markings are non-symmetrical about at least a first axis of the insertable portion;
   wherein, after insertion in the anatomical body, the fiducial markings can be detected by the imaging modality to facilitate unambiguous registration to the anatomical body of the position sensor rigidly held in the insertable portion by correlating the fiducial markings detected by the imaging modality to the determined position of the position sensor in the frame of reference.

2. The apparatus as defined in claim 1 further comprising:
   a fixing mechanism for fixing the insertable portion to the anatomical body;
   wherein, when the insertable portion is inserted into the anatomical body to a location of interest, the fixing mechanism rigidly fixes the insertable portion to a part of the anatomical body near the location of interest; and
   wherein the fiducial markings can be detected while the insertable portion is fixed to the part of the anatomical body near the location of interest.

3. The apparatus as defined in claim 2 further comprising a catheter for inserting the insertable portion into the anatomical body; and
   wherein the fixing mechanism comprises a plurality of longitudinally extending fingers affixed to the insertable portion, each finger having a gripping element for gripping a surface of a passageway near the location of interest, said fixing mechanism having a collapsed configuration where the gripping element is near the catheter, and a deployed configuration where at least one gripping element grips the surface of the passageway; and
   wherein when the fingers are in the deployed configuration, fluid can flow around the catheter and through the passageway.

4. The apparatus as defined in claim 2 wherein the fixing mechanism is selected from the group consisting of a screw for securing the insertable portion to the anatomical body at the location of interest, and at least one barb for rigidly fixing the insertable portion of the catheter to the anatomical body at the location of interest.

5. The apparatus as defined in claim 2 further comprising a catheter for inserting the insertable portion into the anatomical body;
   wherein the fixing mechanism comprises an inflatable member which inflates when the insertable portion is at the location of interest to releasably fix the insertable portion of the catheter to the part of the anatomical body near the location of interest.

6. The apparatus as defined in claim 5 wherein the part of the anatomical body is a passageway near the location of interest; and
   wherein the inflatable member comprises at least one lobe portion, and, wherein, when the at least one lobe portion of the inflatable member is inflated to fix the insertable portion to the part of the anatomical body, fluid can flow around the catheter and through the passageway.

7. The apparatus as defined in claim 6 wherein the at least one lobe portion has a barbed end for engaging a surface of the passageway.

8. The apparatus as defined in claim 1 wherein the imaging modality that can detect the fiducial markings is selected from the group consisting of CT scans, fluoroscopic images and ultrasound images.

9. The apparatus as defined in claim 1 wherein the fiducial markings comprise at least two markings said at least two markings being asymmetrically placed on the insertable portion that permit the position and orientation of the insertable portion to be determined.

10. The apparatus as defined in claim 1 wherein the fiducial markings are not symmetrical about at least the first axis and a second axis of the insertable portion.

11. The apparatus as defined in claim 1 wherein the fiducial markings comprise a mantle which is detectable by the imaging modality and has a shape that is asymmetrical along at least one axis.

12. The apparatus as defined in claim 11 wherein the shape of the mantle is asymmetrical along three axes.

13. The apparatus as defined in claim 11 wherein the mantle is rigidly attached to the position sensor.

14. The apparatus as defined in claim 13 wherein the signal transmitted by the position sensor is indicative of its position and orientation except for a roll axis and wherein the shape of the mantle is symmetric about the roll axis only and otherwise asymmetrical.

15. The apparatus as defined in claim 11 wherein the signal transmitted by the position sensor is indicative of its position and orientation in six degrees of freedom; and
wherein the shape of the mantle is completely asymmetrical.

16. The apparatus as defined in claim 1 further comprising a needle for inserting the insertable portion into the anatomical body, said insertable portion being releasably fixed within the needle.

17. The apparatus as defined in claim 16 further comprising a sensory stylette holding a sensor;
and wherein the insertable portion can be removed from the needle and the sensory stylette inserted while the needle is inserted in the anatomical body.

18. The apparatus as defined in claim 16 wherein the insertable portion holds a first position sensor and a second position sensor longitudinally displaced from the first position sensor.

19. The apparatus as defined in claim 18 further comprising:
at least one zone on a surface of the needle, said at least one zone being longitudinally located between the first position sensor and the second position sensor.

20. The apparatus as defined in claim 16 wherein the fiducial markings comprise at least two markings displaced longitudinally along the insertable portion which permit the position and orientation of the insertable portion to be determined from images obtained by the imaging modality.

21. A method of registering a position sensor to an anatomical body, said method comprising the steps of:
(a) fixing the position sensor to an insertable portion of an apparatus, said insertable portion having non-symmetrical fiducial markings;
(b) inserting the insertable portion of the apparatus to a location of interest in the anatomical body; and
(c) detecting the non-symmetrical fiducial markings on the insertable portion of the apparatus to facilitate registration of the position sensor in the insertable portion to the anatomical body by:
(c1) detecting the non-symmetrical fiducial markings on the insertable portion;
(c2) determining the position of the position sensor in a frame of reference; and
(c3) registering the position sensor to the anatomical body by correlating the detected non-symmetrical fiducial markings to the determined position of the position sensor in the frame of reference.

22. The method as defined in claim 21 further comprising:
(i) detecting the non-symmetrical fiducial marking to determine a position, orientation and direction of the insertable portion in image space;
(ii) determining the position and orientation of the position sensor along at least two axes in the frame of reference; and
(iii) registering the position sensor to the anatomical body by correlating the determined position, orientation and direction of the insertable portion from the detected non-symmetrical fiducial markings to the determined position and orientation of the position sensor in the frame of reference.

23. A device for facilitating tracking of an apparatus in an anatomical body, said device comprising:
an insertable portion holding a position sensor that can transmit a position signal indicative of its position in a frame of reference;
non-symmetrical fiducial markings on the insertable portion, said non-symmetrical fiducial markings being detectable by an imaging modality to facilitate unambiguous registration of the position sensor held in the insertable portion to the anatomical body; wherein the apparatus can insert the insertable portion into the anatomical body, and, the position signal transmitted from the position sensor indicates the position of the apparatus near the position sensor;
wherein the insertable portion substantially rigidly holds the sensor at a known spatial position with respect to the non-symmetrical fiducial markings; and
wherein, after insertion of the insertable portion in the anatomical body, an image of the insertable portion can be obtained by the imaging modality, and, the position sensor can be registered to the anatomical body by correlating the non-symmetrical fiducial markings detected by the imaging modality to the determined position of the position sensor in the frame of reference.

24. The device as defined in claim 23 wherein the insertable portion further comprises:
(i) a stylette hub which mates with a needle hub associated with the needle for orienting the hollow stylette with the needle; and
(ii) a stylette plug for preventing entry of tissue into the hollow stylette during insertion into the anatomical body.

25. The device as defined in claim 24 wherein mating the needle hub with the stylette hub releasably fixes the hollow stylette to the needle.

26. The device as defined in claim 23 wherein the apparatus comprises a catheter and the insertable portion is rigidly fixed to the catheter.

* * * * *